(12) United States Patent
Shibata et al.

(10) Patent No.: US 11,690,961 B2
(45) Date of Patent: Jul. 4, 2023

(54) CAP FOR SYRINGE NEEDLE AND DEVICE FOR DIALYSIS CIRCUIT PRIMING

(71) Applicants: Artisan Lab Co., Ltd., Kanagawa (JP); Nipro Corporation, Osaka (JP)

(72) Inventors: Kazuhiko Shibata, Kanagawa (JP); Hiroyuki Nakagami, Osaka (JP); Tatsuya Kudo, Osaka (JP); Naoya Kataoka, Osaka (JP)

(73) Assignees: ARTISAN LAB CO., LTD., Kanagawa (JP); NIPRO CORPORATION, Osaka (JP)

(*) Notice: Subject to any disclaimer, the term of this patent is extended or adjusted under 35 U.S.C. 154(b) by 544 days.

(21) Appl. No.: 16/595,176

(22) Filed: Oct. 7, 2019

(65) Prior Publication Data
US 2020/0038596 A1   Feb. 6, 2020

Related U.S. Application Data

(63) Continuation of application No. PCT/JP2018/014775, filed on Apr. 6, 2018.

(30) Foreign Application Priority Data

Apr. 7, 2017 (JP) ................. 2017-077074
Jun. 30, 2017 (JP) ................. 2017-129165

(51) Int. Cl.
*A61M 5/32* (2006.01)
*A61M 1/36* (2006.01)
(Continued)

(52) U.S. Cl.
CPC ........ *A61M 5/3202* (2013.01); *A61M 1/3649* (2014.02); *A61M 5/001* (2013.01);
(Continued)

(58) Field of Classification Search
CPC ............. A61M 5/3202; A61M 1/3649; A61M 1/3643; A61M 2039/1061; A61M 39/1011; A61M 2039/1016; A61M 39/14
See application file for complete search history.

(56) References Cited

U.S. PATENT DOCUMENTS 4,654,034 A * 3/1987 Masters .............. A61M 5/3271
604/263
5,951,870 A 9/1999 Utterberg
(Continued)

FOREIGN PATENT DOCUMENTS

CN 102245226 A 11/2011
EP 0305364 B2 1/1998
(Continued)

OTHER PUBLICATIONS

Extended European Search Report dated Nov. 13, 2020, issued in counterpart European Patent Application No. 18780813.4 (7 pages).
(Continued)

*Primary Examiner* — Theodore J Stigell
*Assistant Examiner* — Rachel T. Smith
(74) *Attorney, Agent, or Firm* — Quarles & Brady LLP

(57) ABSTRACT

A needle cap and a dialysis circuit priming device with increased safety and convenience in the cleaning and priming of a blood circuit are provided. According to the present invention, a needle cap is provided including two needle connecting parts, and a flow path connecting the two needle connecting parts. A dialysis circuit priming device is also provided including two needles, two needle connecting parts each arranged with the two needles respectively, and a flow path for connecting the two needle connecting parts.

9 Claims, 18 Drawing Sheets

(51) Int. Cl.
*A61M 5/00* (2006.01)
*A61M 5/158* (2006.01)
*A61M 5/24* (2006.01)

(52) U.S. Cl.
CPC .......... *A61M 5/158* (2013.01); *A61M 5/3295* (2013.01); *A61M 2005/2488* (2013.01)

(56) References Cited

U.S. PATENT DOCUMENTS

| | | | | |
|---|---|---|---|---|
| 6,824,524 | B1 * | 11/2004 | Favre .................. | A61M 1/3627 604/28 |
| 2003/0028156 | A1 * | 2/2003 | Juliar .................... | A61M 39/10 604/310 |
| 2011/0166532 | A1 * | 7/2011 | Brandenburger ..... | A61J 1/2096 604/201 |
| 2011/0213289 | A1 | 9/2011 | Toyoda et al. | |

FOREIGN PATENT DOCUMENTS

| | | | |
|---|---|---|---|
| JP | H61-037168 | | 2/1986 |
| JP | 2577940 | B2 | 2/1997 |
| JP | 2001-520101 | A | 10/2001 |
| JP | 2002-537907 | A | 11/2002 |
| JP | 2009-89841 | * | 4/2009 |
| JP | 2009-089841 | A | 4/2009 |
| JP | 200989841 | A * | 4/2009 |
| JP | 2010-279494 | A | 12/2010 |
| JP | 2012-139405 | A | 7/2012 |
| JP | 2012139405 | A * | 7/2012 |
| WO | 1988/06460 | A1 | 9/1988 |
| WO | WO-8806460 | A * | 9/1988 .......... A61M 1/3643 |
| WO | WO-8806460 | A1 * | 9/1988 .......... A61M 1/3672 |
| WO | 1999/20376 | A1 | 4/1999 |
| WO | 2000/051664 | A1 | 9/2000 |

OTHER PUBLICATIONS

International Search Report and Written Opinion dated Jul. 10, 2018, for PCT Application No. PCT/JP2018/014775.
English translation of Written Opinion issued in International Application No. PCT/JP2018/014775, dated Jul. 10, 2018, 8 pages.
Office Action dated Dec. 29, 2021 issued in CN Appl. No 201880023125.2 (15 pages) (including English Translation).
Office Action dated Feb. 1, 2022 issued in IN Appl No. 201917045032 (5 pages) (including English Translation) .
Office Action dated Sep. 5, 2022 issued in CN Appl. No. 201880023125. 2, with English translation attached. (13 pages).

* cited by examiner

Fig. 7A
Fig. 7B
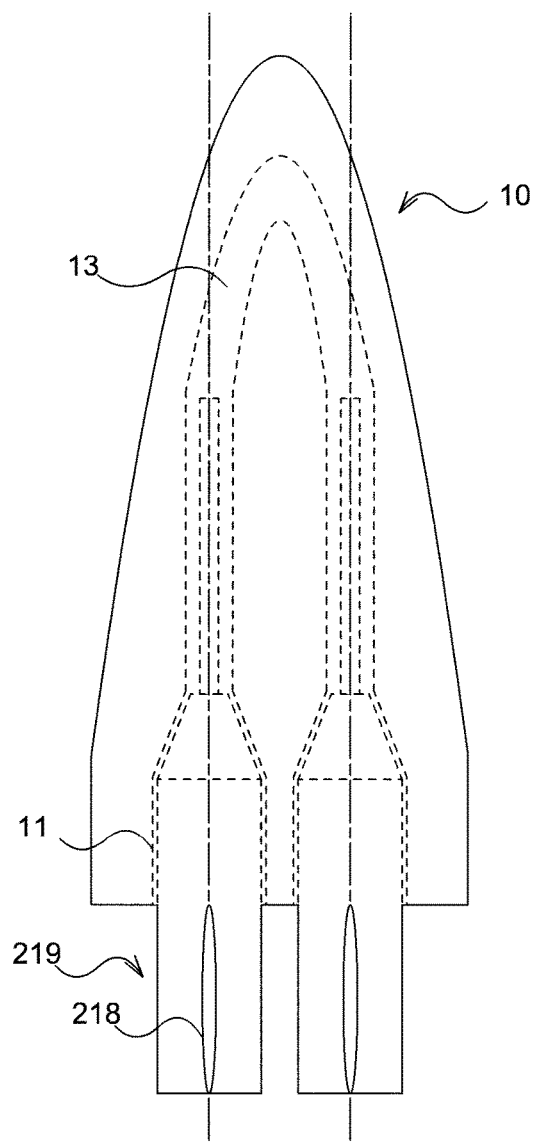
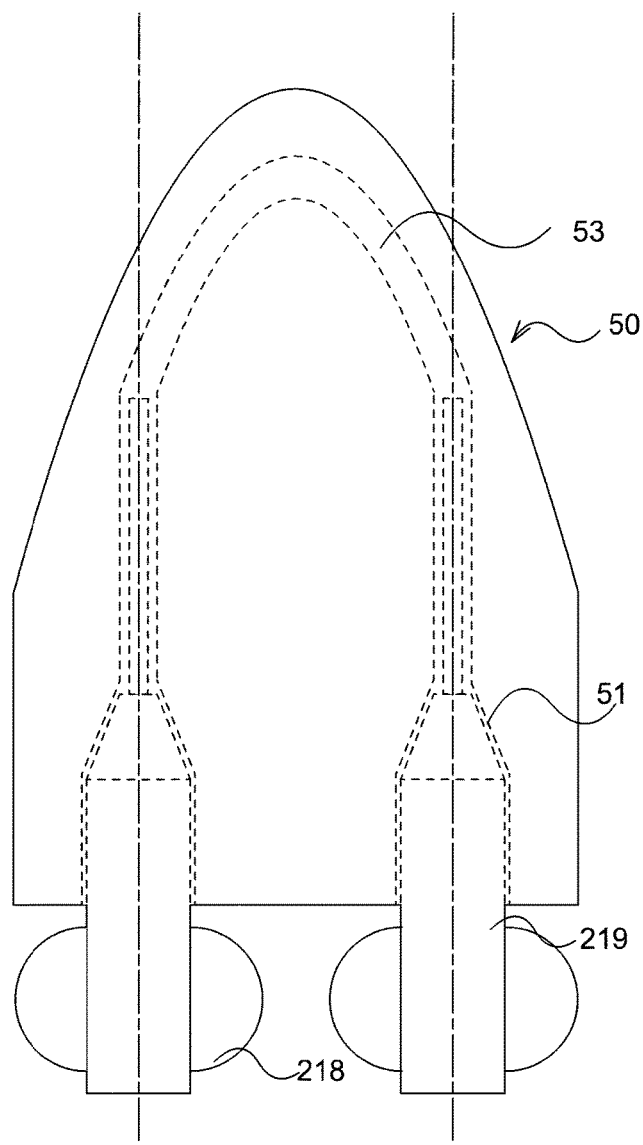

Fig. 9A
Fig. 9B
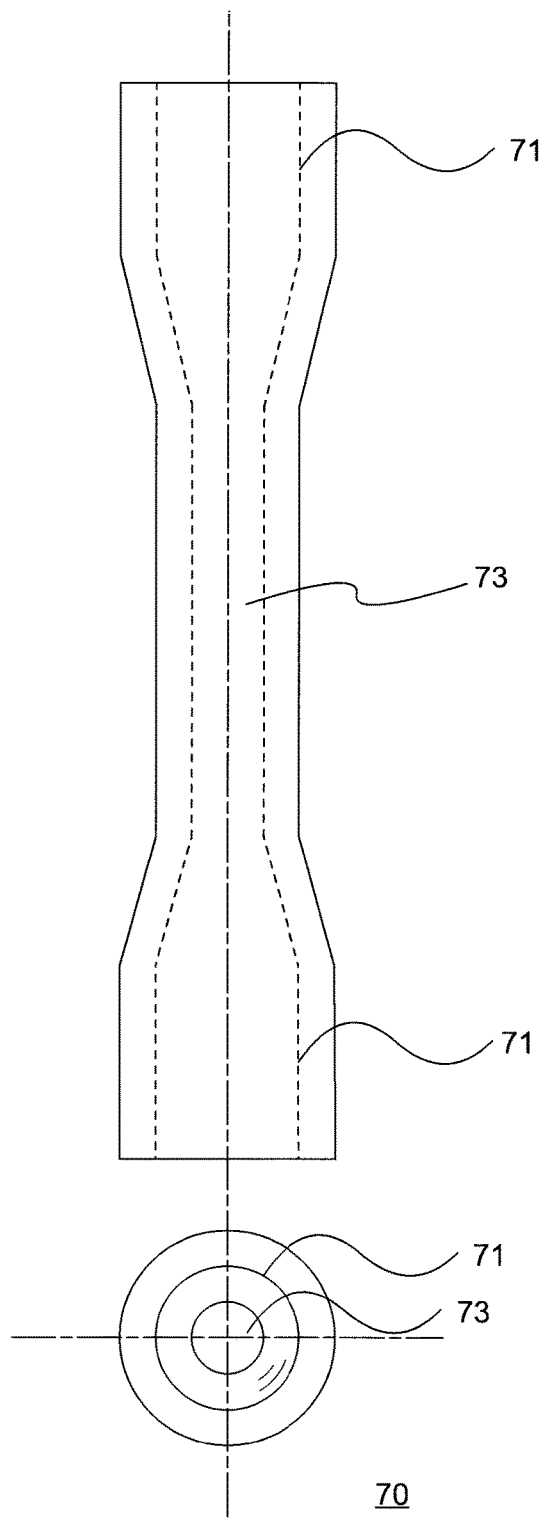
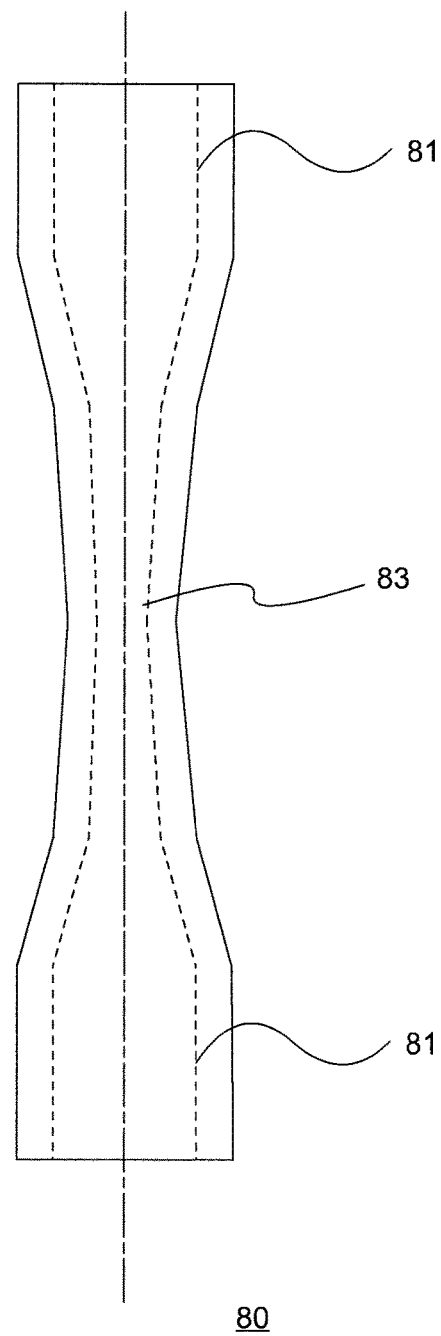

Fig. 10A
Fig. 10B
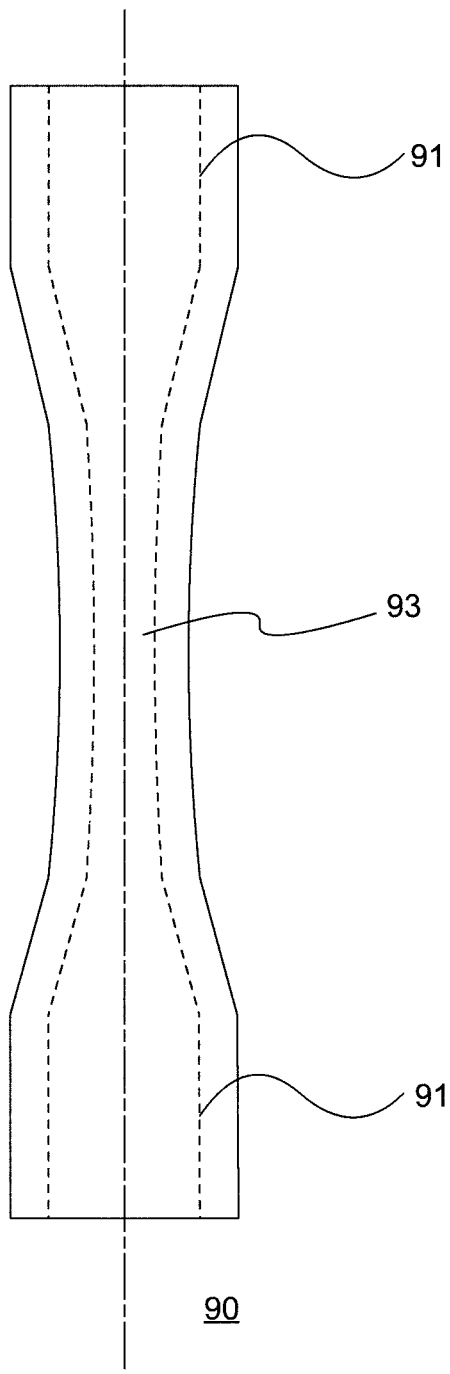
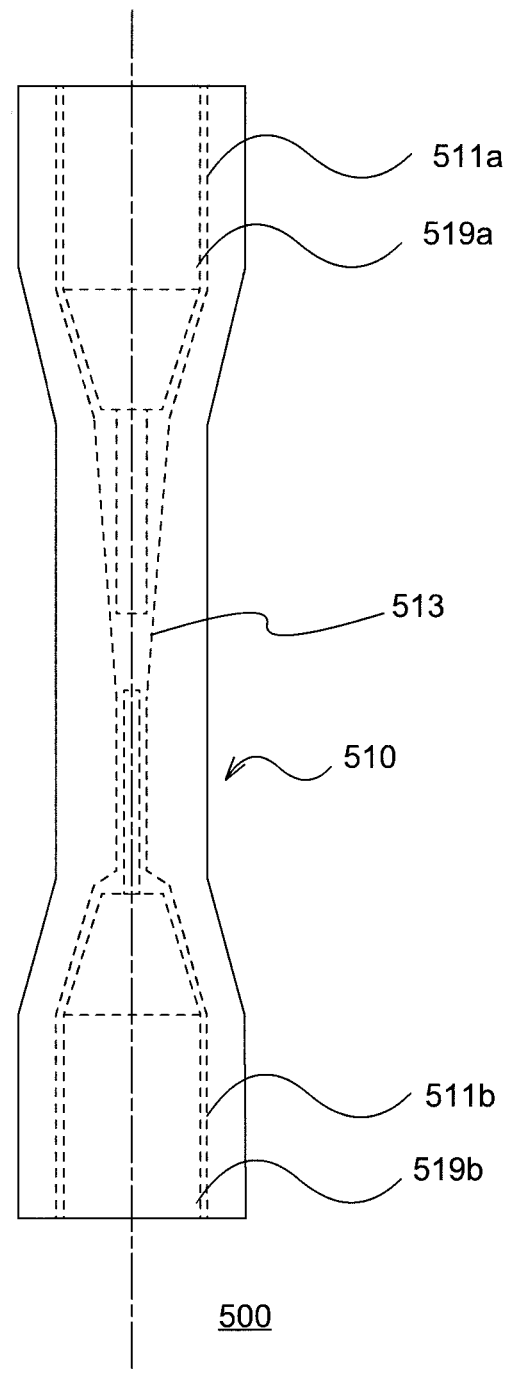

Fig. 11A
Fig. 11B
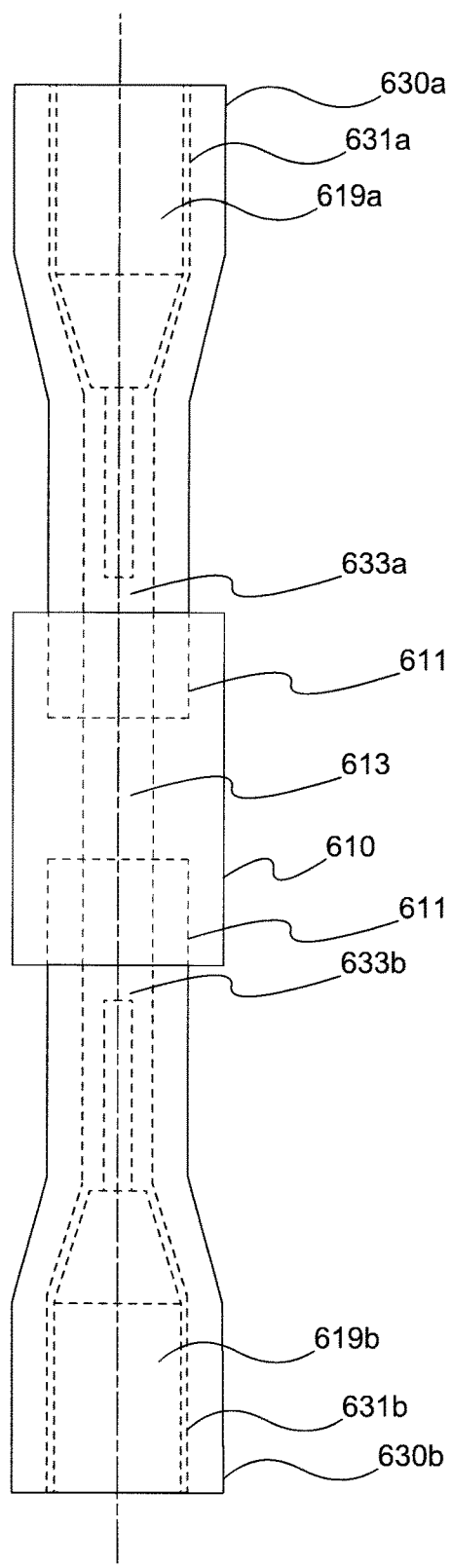
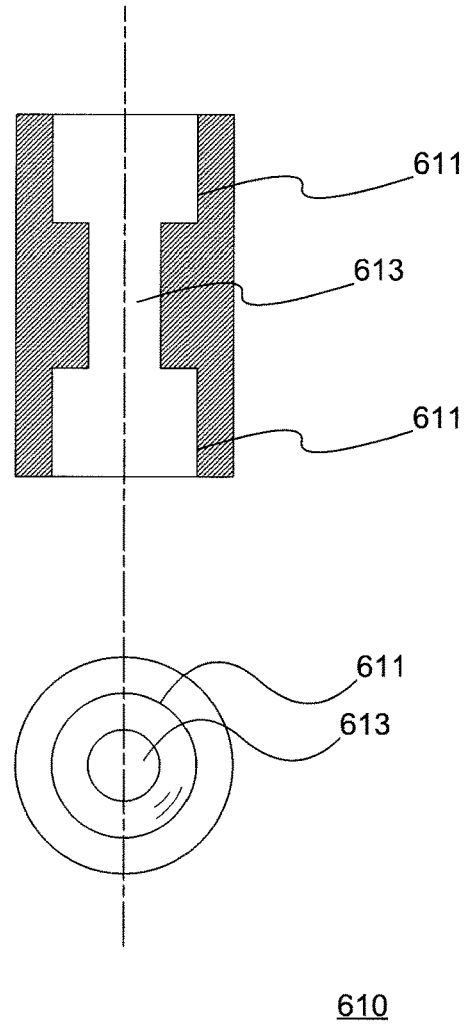

CAP FOR SYRINGE NEEDLE AND DEVICE FOR DIALYSIS CIRCUIT PRIMING

CROSS REFERENCE TO RELATED APPLICATIONS

This application is a continuation of PCT Application No. PCT/JP2018/014775, filed on Apr. 6, 2018, and claims the benefit of priority from the prior Japanese Patent Application No. 2017-077074, filed on Apr. 7, 2017, and the prior Japanese Patent Application No. 2017-129165, filed on Jun. 30, 2017, the entire contents of which are incorporated herein by reference.

FIELD

The present invention relates to a cap for injection needles and a device for dialysis circuit priming.

BACKGROUND

When a renal function is reduced it is necessary to remove uremic toxins from the blood. As a result, blood dialysis has become a global mainstream treatment for removing uremic toxins from the blood. In a blood dialysis, two needles are inserted into a blood vessel, uremic toxins are removed by extracting blood via a tube connected to one of the needles and passing the blood through a dialyzer, and returning the blood into the body via a tube connected to the other needle. A dialysis blood circuit is one route which is closed, and it is necessary to fill up the route with saline or dialysate at the start of dialysis. The artery side access part (arterial side) which is used in the following explanation means a bonding part between an artery side circuit and an artery side vascular access device, and a vein side access part (venous side) means a bonding part between a vein side circuit and a vein side vascular access device.

In order to remove fine dust within a dialyzer and a blood circuit, remove a film protective agent and remove a filling liquid and air by washing and return it to a state in which the treatment can be started, it is necessary to prepare the circuit before starting dialysis and perform cleaning in the blood circuit and priming the blood circuit. Cleaning and priming are performed according to the method described in the instruction manual of the dialyzer. This work is preferably carried out immediately before starting dialysis, and has been conventionally performed by the hand of the medical practitioner by the method described below.

The dialyzer and a blood circuit are properly connected. At this time, it is important to not touch the connection of the blood circuit and the dialyzer with hands or forceps. The artery side blood circuit is filled with saline using a saline container connected to a priming line or a replacement fluid line or a replacement fluid line that is connected with a hemodialysis machine. Next, the vein side blood circuit is connected in the venous side of the dialyzer. The order this task is performed in may be changed according to the type of dialyzer in order to prevent air contamination. When all connections are finished, the dialyzer and blood circuit are flushed with saline and cleaned. After cleaning is completed, the inside of the blood circuit and the dialyzer are replaced with filling saline, and a soft packed saline for rehydration and returning blood after replacement is substituted. The cleaning and priming operation is performed by skilled staff who sufficiently understands the concept of hygiene in medicine.

Today's dialysis monitoring devices have evolved in which a method for creating a closed circuit by connecting two routes of an arterial side and a venous side to be connected to the patient, and automatically filling with saline or dialysate has become mainstream. By this method, it is possible to securely clean the dialyzer. However, since the two routes (tubes) of the arterial side and venous side are connected when dialysis is started, it is necessary to separate them and connect a needle respectively.

For example, Japanese Laid Open Patent Publication No. 2012-139405 describes a blood cleaning device arranged with a Y shaped tube which can be connected to a drain line and in which an artery side needle connection end and a vein side needle connection end are mutually connected to a drain path.

SUMMARY

It is desirable to safely and conveniently perform attachment of a needle after cleaning and priming of a blood circuit from the viewpoint of reducing the workload burden of medical staff, needle penetration accidents and the risk of infections.

The present invention has been made to solve the problems described above and provides a needle cap and a dialysis circuit priming device with increased safety and convenience in the cleaning and priming of a blood circuit.

According to one embodiment of the present invention, a needle cap is provided including two needle connecting parts, and a flow path connecting the two needle connecting parts.

The needle cap may also include a weak part in the two needle connecting parts.

The needle cap may also include a film arranged in the needle connecting part for sealing the flow path.

The needle cap may also include a threaded part in the needle connecting part.

The needle cap may also include a locking part for locking an infusion stand.

In addition, according to one embodiment of the invention, a dialysis circuit priming device is provided including two needles, two needle connecting parts each arranged with the two needles respectively, and a flow path for connecting the two needle connecting parts.

The dialysis circuit priming device may also include a weak part in the two needle connecting parts.

The dialysis circuit priming device may also include a film arranged in the needle connecting part for sealing the flow path.

The dialysis circuit priming device may also include a threaded part arranged respectively on the two needles and the needle connecting part, wherein the two needles are screwed into the needle connecting parts.

The dialysis circuit priming device may also include a locking part for locking an infusion stand.

The dialysis circuit priming device may also include a butterfly shaped needle.

In addition, according to one embodiment of the present invention, a dialysis circuit priming device is provided including a first injection needle cap and a second injection needle cap arranged with a needle and a needle connecting part arranged with the needle, a joint member locking the first needle cap and the second needle cap, and a flow path connected to two of the needle connecting parts.

The dialysis circuit priming device may also include a thread arranged on a tip end part of the first needle cap and the second needle cap, wherein a joint part of the joint member for locking the first needle cap and the second needle cap is arranged with a thread.

BRIEF DESCRIPTION OF DRAWINGS

FIG. 7A is a schematic diagram of the dialysis circuit priming device 100 according to one embodiment of the present invention.

FIG. 7B is a schematic diagram of a dialysis circuit priming device 300 according to one embodiment of the present invention.

FIG. 9A is a schematic diagram of a needle cap 70 according to one embodiment of the present invention.

FIG. 9B is a schematic diagram of a needle cap 80 according to one embodiment of the present invention.

FIG. 10A is a schematic diagram of a needle cap 90 according to one embodiment of the present invention.

FIG. 10B is a schematic diagram of dialysis circuit priming device 500 according to one embodiment of the present invention.

FIG. 11A shows a dialysis circuit priming device 600.

FIG. 11B shows a cross sectional diagram taken along a center line of FIG. 11A (upper diagram) and a side surface diagram as seen from the center line direction (lower diagram).

Figure 1:
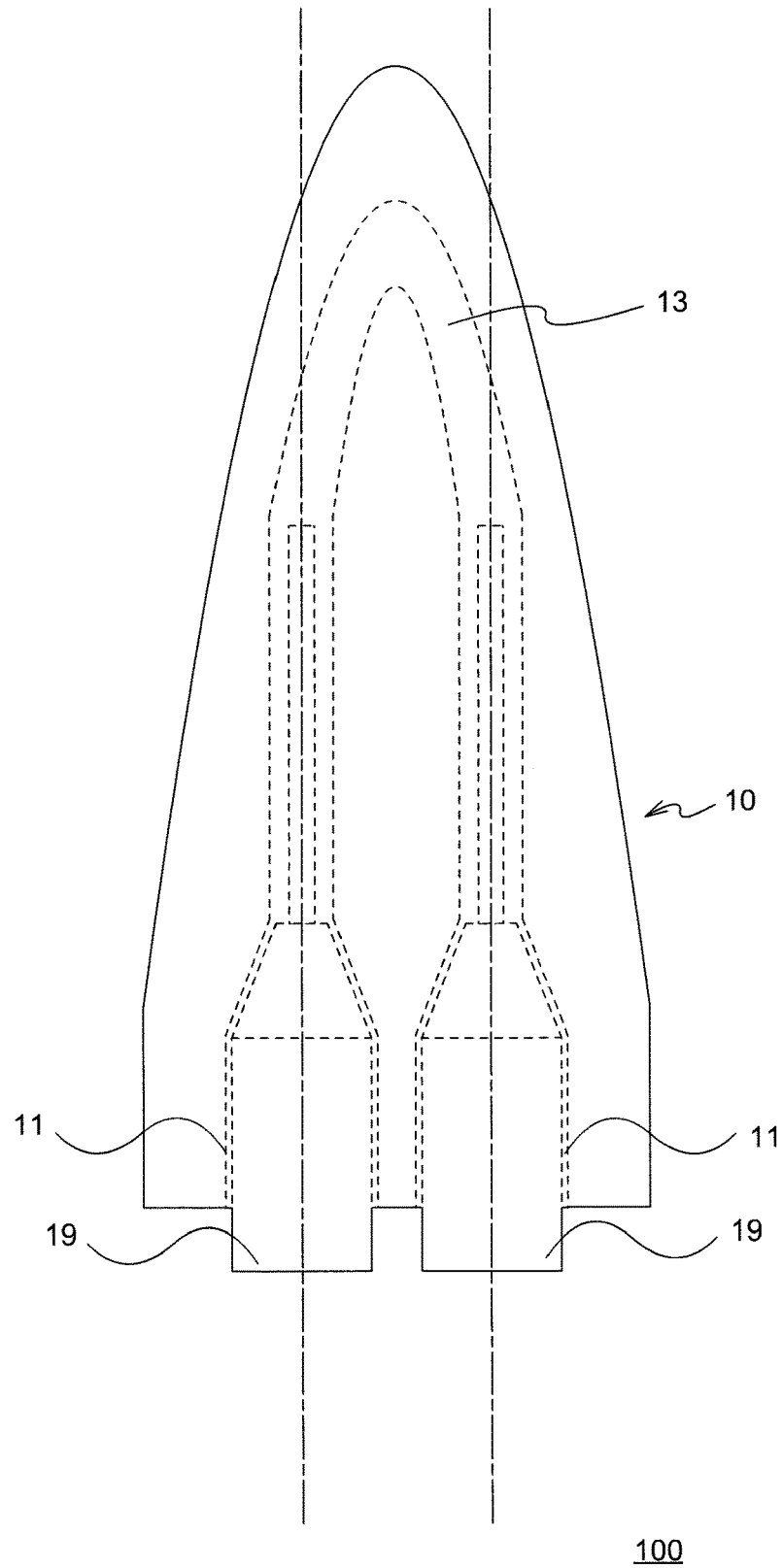
FIG. 1 is a schematic diagram of a dialysis circuit priming device 100 according to one embodiment of the present invention.

REFERENCE SIGNS LIST 10 needle cap, 11 needle connecting part, 13 flow path, 19 needle, 20 needle cap, 21 needle connecting part, 23 flow path, 25 film, 30 needle cap, 31 needle connecting part, 33 flow path, 35 threaded part, 40 needle cap, 41 needle connecting part, 43 flow path, 45 locking part, 50 needle cap, 51 needle connecting part, 53 flow path, 60 needle cap, 61a needle connecting part, 61b needle connecting part, 63 flow path, 69a thick needle, 69b thin needle, 70 needle cap, 71 needle connecting part, 73 flow path, 80 needle cap, 81 needle connecting part, 83 flow path, 90 needle cap, 91 needle connecting part, 93 flow path, 100 dialysis circuit priming device, 200 dialysis circuit priming device, 218 wing part, 219 butterfly needle, 300 dialysis circuit priming device, 400 dialysis circuit priming device, 500 dialysis circuit priming device, 510 needle cap, 511a needle connecting part, 511b needle connecting part, 513 flow path, 519a thick needle, 519b thin needle, 600 dialysis circuit priming device, 610 joint member, 611 locking part 613, flow path, 619 needle, 619a needle, 619b needle, 633 flow path, 633a flow path, 633b flow path, 700 dialysis circuit priming device, 710 joint member, 711 locking part, 713 flow path, 719 needle, 719a needle, 719b needle, 733 flow path, 733a flow path, 733b flow path, 735 threaded part, 800 dialysis circuit priming device, 800a dialysis circuit priming device, 812 weak part, 813 flow path, 813a drain path, 818a wing part, 818b wing part, 819 needle, 819a needle body, 819b needle hub, 830 tube, 831 connector, 833 cap, 835 cap, 840 robert clamp, 870 branch tube, 871 first end part, 873 second end part, 875 third end part, 1010 priming liquid container, 1020 blood dialyzer, 1030 artery chamber, 1050 vein chamber, 1060 pump, 1111 priming liquid supply line, 1120 line, 1121 artery side connection part, 1130 line, 1140 line, 1150 line, 1160 line, 1161 vein side connection part, 1170 line, 1171 valve

DESCRIPTION OF EMBODIMENTS

A needle cap and a dialysis circuit priming device according to the present invention is explained herein while referring to the drawings. The cap for injection needles and dialysis circuit priming device according to the present invention should be construed as being limited to the described contents of the embodiments below. Furthermore, in the drawings referred to in the present embodiment, the same parts or parts which have similar functions are denoted by the same reference numerals and a repeated explanation thereof is omitted.

FIG. 1 is a schematic diagram of a dialysis circuit priming device 100 according to one embodiment of the present invention. The dialysis circuit priming device 100 is arranged with a needle cap 10 which includes a flow path 13 connected to two needle connecting parts 11 each arranged with a needle 19 respectively. The needle 19 may be a puncturing needle comprised from an outer needle and an inner needle which are commonly used for in blood dialysis, or may be a butterfly needle or the like. By arranging a flow blocking means such as a clamp to the flow path 13, it is possible to prevent the mixing of air into one of the needles 19 and the dialysis circuit even after removing the other needle 19.

Figure 3:
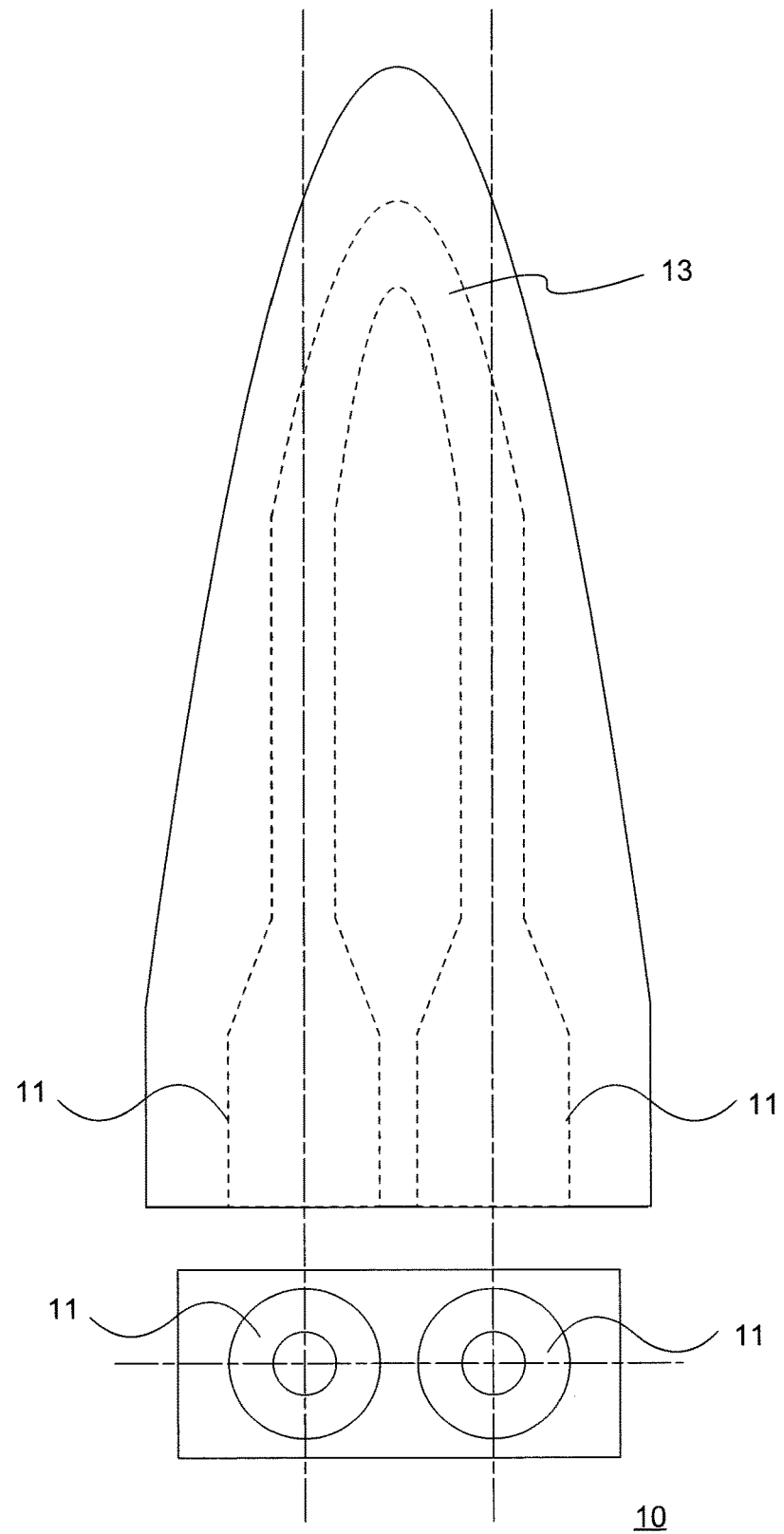
FIG. 3 is a schematic diagram of a needle cap according to one embodiment of the present invention.

FIG. 3 is a schematic diagram of a needle cap 10, the upper part shows an upper view of the needle cap 10, and the lower part shows a side view viewed from the needle connecting part 11 side. The needle cap 10 is, for example, made from a resin and can be formed by a known resin used for medical needle caps. In addition, the resin which forms the flow path 13 preferably has flexibility. By providing the flow path 13 with flexibility, in the case when the needle 19 and the flow path 13 are filled with saline, by clamping the flow path 13, it is possible to prevent air from entering the one needle 19 even when the other needle 19 is removed from the needle cap 10. In the needle cap 10 according to the present invention, the flow blocking means is not limited thereto, and a valve (not shown in the diagram) may be arranged in the flow path 13.

In addition, it is sufficient that the flow path 13 has a length which allows the needle connecting part 11 to be connected and the length of the flow path 13 is not particularly limited. The flow path 13 may further include an air reservoir.

In addition, the needle connecting part 11 has a shape corresponding to the shape of the needle 19 and adhesion to the needle 19 is imparted to the needle cap 10. In addition, the needle connecting part 11 may also have a contact surface with the needle 19 having elasticity in order to improve adhesion with the needle 19. Although two needles 19 are shown in FIG. 1 having the same thickness, the present invention is not limited thereto, and the needles may each have different thickness.

Figure 8:
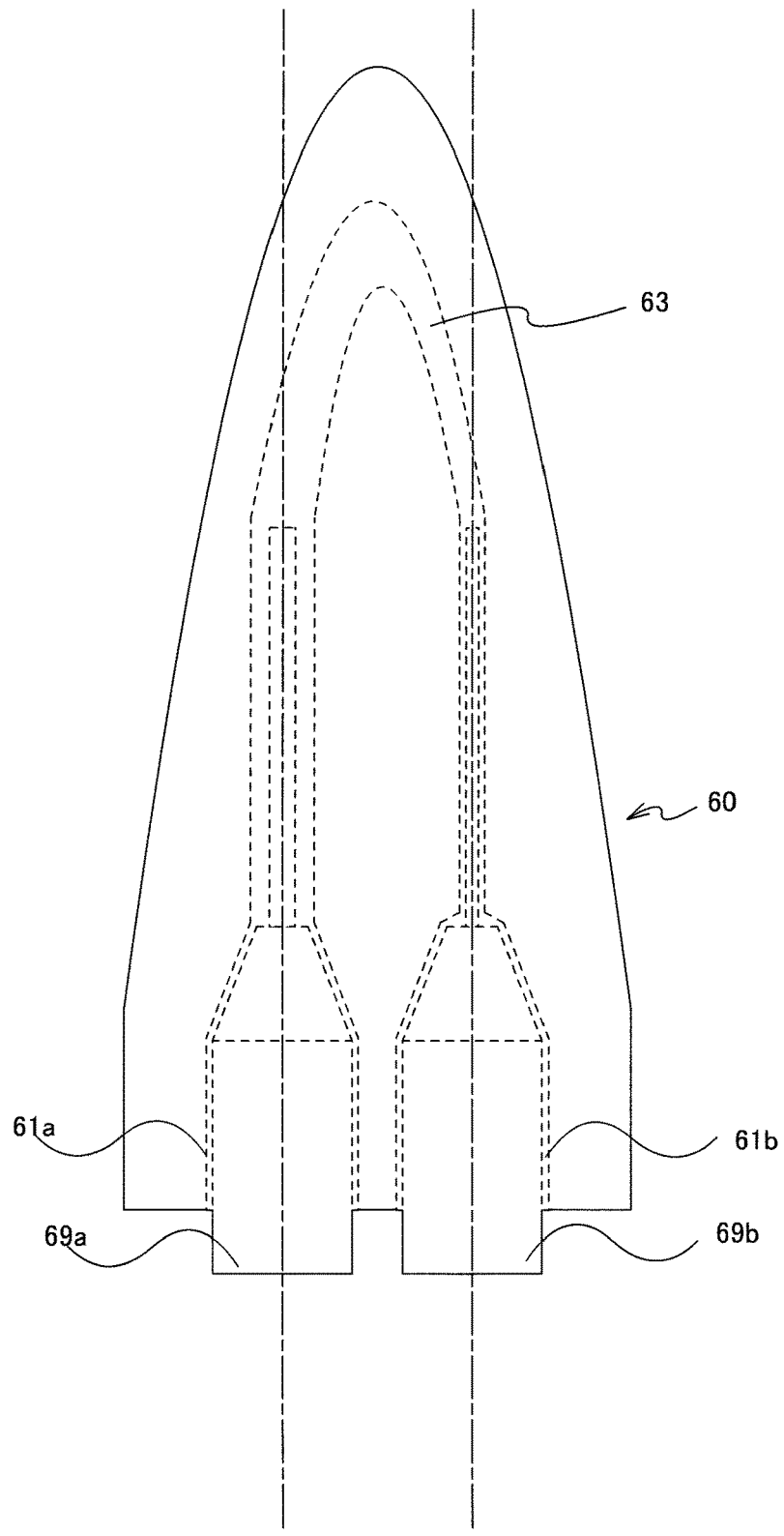
FIG. 8 is a schematic diagram of a dialysis circuit priming device 400 according to one embodiment of the present invention.

In addition, for example, it is possible to use the dialysis circuit priming device 400 shown in FIG. 8 as a modified example in which each needle has a different thickness. The dialysis circuit priming device 400 is arranged with a needle 69a and a needle 69b having different thicknesses in a needle cap 60. In FIG. 8, as an example, a thick needle 69a is arranged on a needle connecting part 61a, and a thin needle 69b is arranged on a needle connecting part 61b. Here, since the flow path 63 connects the needle connecting part 61a having a thick needle 69a and the needle connecting part 61b having a thin needle 69b, a structure may be provided in which the diameter decreases toward the needle connecting part 61b from the needle connecting part 61a.

In addition, if the needle cap 10 has a structure including the flow path 13 connected to the two needle connecting parts 11, then the outer shape is not particularly limited, but from the view point of needle accident prevention, it is preferred that the needle cap 10 has a structure in which the two needles 19 are arranged in parallel or substantially parallel. When the two needles 19 have such an arrangement, it is possible to provide a handle part on the side where the needles 19 of the needle cap 10 are arranged, improving retention when inserting and removing the needle 19, and it is possible to prevent needle accidents. Therefore, it is preferred to provide a sufficient size so that a user can hold the needle cap 10 on the side where the needles 19 of the needle cap 10 are arranged.

(BLOOD CIRCUIT CLEANING AND PRIMING)

Figure 2:
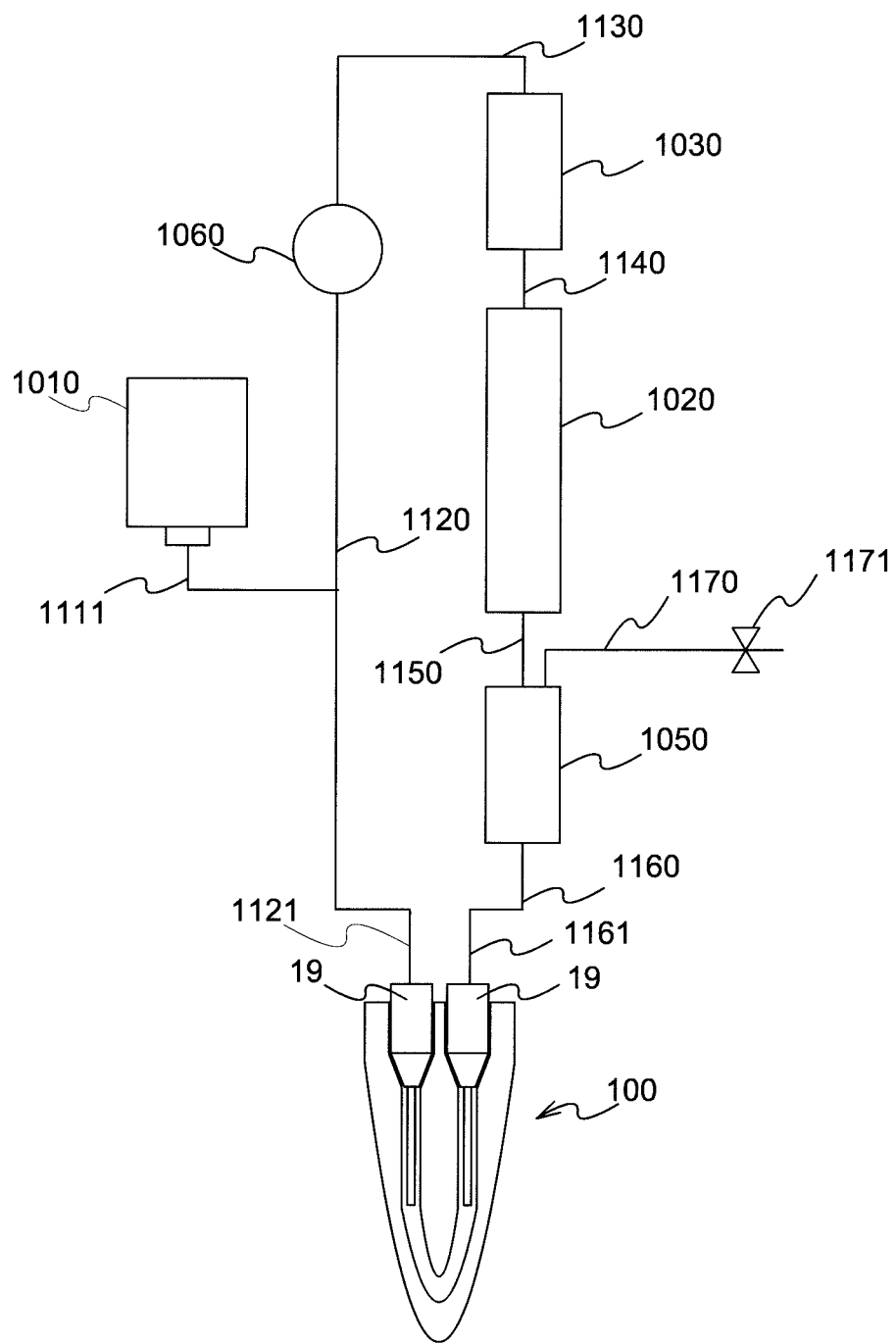
FIG. 2 is a schematic diagram for explaining a priming method using the dialysis circuit priming device 100 according to one embodiment of the present invention.

A cleaning and priming method of a blood circuit using the dialysis circuit priming device 100 according to the present invention is explained while referring to FIG. 2. FIG. 2 is a schematic diagram for explaining a priming method using the dialysis circuit priming device 100 according to one embodiment of the present invention. Since it is possible to use a blood circuit which is commercially available for medical use, although a detailed explanation is omitted, in recent years there have been cases where a dialysate is supplied from a dialysis monitoring device or when pressure is applied to a dialysate connected to dialyzer and a priming solution is supplied into the blood circuit by reverse filtration, it is also possible to use the dialysis circuit priming device according the present invention for any method. A general method conventionally performed is described as an example. For example, a priming liquid container 1010, a blood dialyzer 1020, an artery chamber 1030, a vein chamber 1050 and a pump 1060 are arranged.

The priming liquid container 1010 is connected to a line 1120 between an artery side connection part 1121 and the artery chamber 1030 through a priming liquid supply line 1111. The blood dialyzer 1020 is connected to the artery chamber 1030 via a line 1140 and connected to the vein chamber 1050 via a line 1150. The artery chamber 1030 is connected to one of the needles 19 arranged in the dialysis circuit priming device 100 through the vein side connection part 1161 of the line 1130. The vein chamber 1050 includes a line 1170 which drains a priming solution from the close blood circuit. The line 1170 is arranged with a valve 1171 and the priming solution can be drained from the blood circuit by opening the valve. In addition, the vein chamber 1050 is connected to the other of the needles 19 arranged in the dialysis circuit priming device 100 via a line 1160. Furthermore, although an example in which the pump 1060 is arranged in the artery chamber 1030 side (arterial side blood circuit) is shown in FIG. 2, the present invention is not limited to this arrangement and the blood dialysis device in which the pump 1060 is arranged in the vein chamber 1050 side (artery side blood circuit) may be used.

After the blood circuit is connected, saline or dialysate and the like is supplied from the priming liquid container 1010 when the pump 1060 rotates. While a supplied liquid fills the artery chamber 1030, the blood dialyzer 1020 and the vein chamber 1050, it is possible for the liquid to flow around the closed circuit via a flow path (flow path 13 in FIG. 1) created by the present invention and perform washing and circuit filling. It is possible to discard the air and washed liquid within the circuit by discharging the air and injected liquid from the circuit through a tube from the vein chamber 1050 to the exterior of the circuit.

The cleaning procedure of a blood circuit is carried out according to the operation procedure of a blood dialysis apparatus and blood circuit which are used. By using the dialysis circuit priming device 100 according to the present invention, it is possible to perform priming via the flow path 13 in a state in which it is connected with the needle 19, and it is possible to puncture the needle 19 in a dialysis patient after priming and start blood dialysis immediately. As a result, by simply connecting the dialysis circuit priming device 100 to a blood circuit, it is not necessary to perform an attachment operation of a needle after priming, and it is possible to provide a simple operation to users.

In addition, the liquid in the circuit is generally extracted and discarded after the completion of the dialysis. In this case, after completion of the dialysis, it is necessary to extract saline or dialysate remaining in the blood circuit due to blood return from the blood circuit. As a result, conventionally, it was necessary to remove the two needles and connect the ends at the artery side and vein side in the blood circuit to each other. As a result, it is desirable to safely and conveniently perform the removal of needles when performing an extraction operation after completion of the blood dialysis and a reconnection operation of the artery side blood circuit and the vein side blood circuit. As a result, in one embodiment, a needle cap and a dialysis circuit priming device are provided with increased safety and convenience during an extraction operation after completion of a blood dialysis. In one embodiment, it is possible to perform an extraction process by again returning both needles to the device according to the present invention. Following this, it is possible to prevent the needle accidents which are likely to occur during a process such as removing the needle by cutting a tube connected to the device of present invention with scissors or the like. According to the present invention, it is also possible to provide a needle cap and a dialysis circuit priming device with increased safety and convenience during an extraction operation after completion of blood dialysis.

Figure 4:
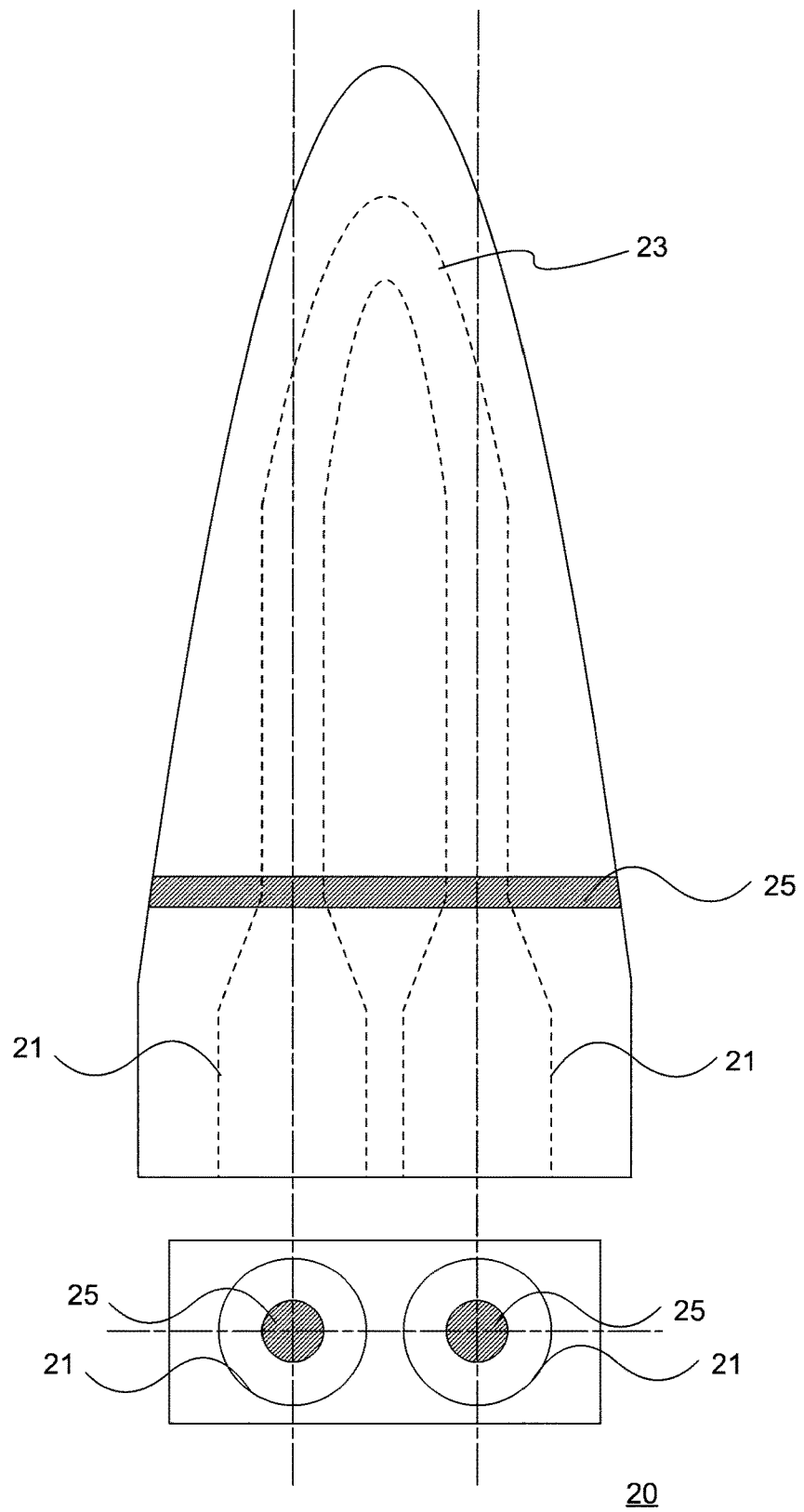
FIG. 4 is a schematic diagram of a needle cap according to one embodiment of the present invention.

The needle cap according to the present invention is further explained. FIG. 4 is a schematic diagram of a needle cap 20 according to one embodiment of the present invention. The needle cap 20 includes a flow path 23 which is connected to two needle connecting parts 21. In addition, the needle cap 20 is different from the needle cap 10 in that a film 25 for sealing the flow path 23 is arranged on the needle connecting part 21.

Since it is possible to use a known film which is used for a vial for injection liquids as the film 25, a detailed explanation is omitted. In addition, although a structure is shown in FIG. 4 in which the film 25 is arranged on the entire surface of a cross section in a perpendicular direction to which the needle is inserted in the needle connecting part 21, the present embodiment is not limited to this and the film 25 may be arranged on only a cavity part of the needle connecting part 21. In the needle cap 20, the film 25 is a flow blocking means which replaces a valve explained using the needle cap 20. By providing the film 25, in the case when the needle 19 and the flow path 13 are filled with a saline, even when one needle 19 is removed from the needle cap 10, it is possible to block air entering into the flow path 23 by the film 25, and prevent air entering the other needle 19. Since the remaining structure is the same as the needle cap 10 described above, a detailed explanation is omitted. It is also possible to apply the modified example having needles each with different thickness described above.

Figure 5:
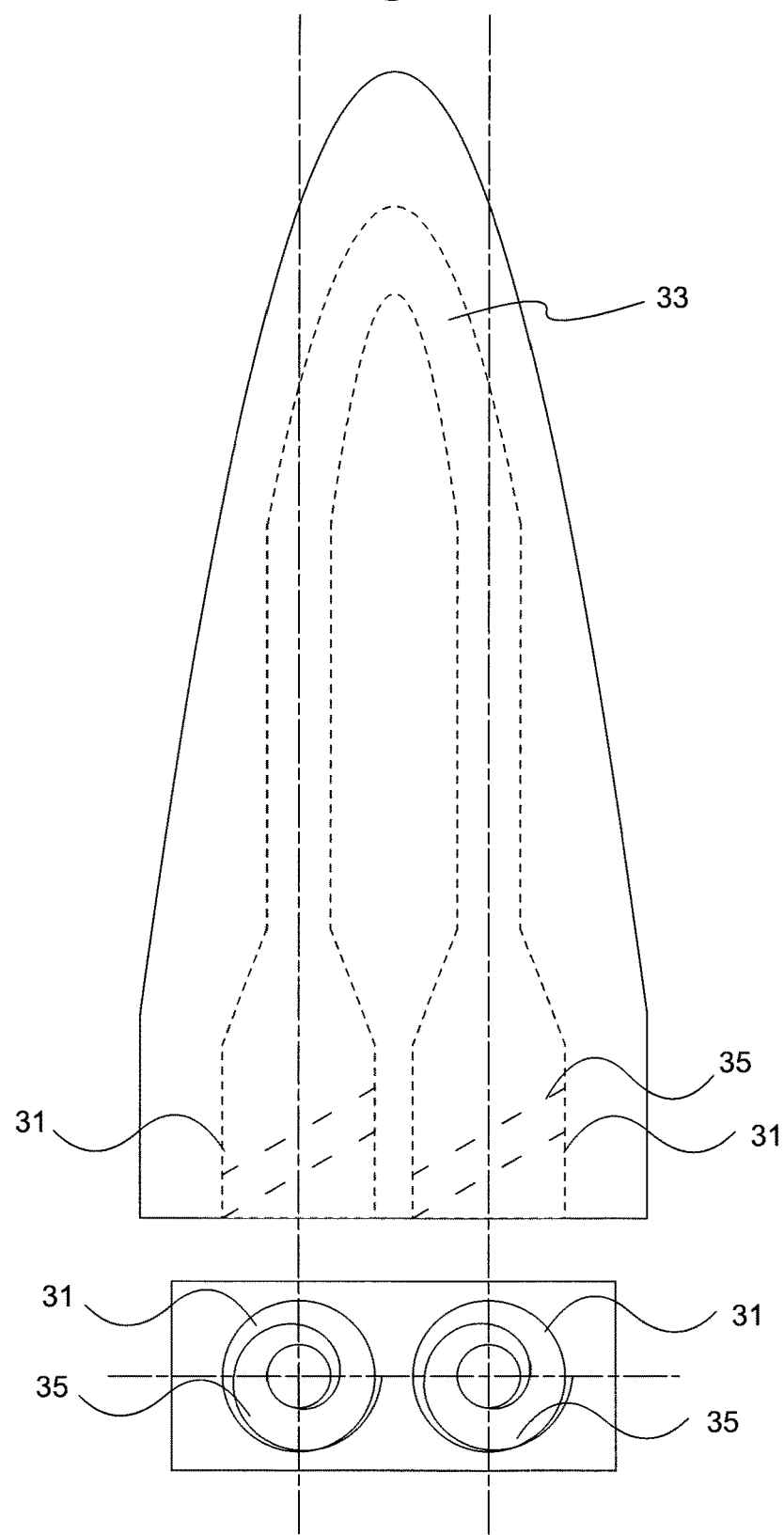
FIG. 5 is a schematic diagram of a needle cap according to one embodiment of the present invention.

FIG. 5 is a schematic diagram of a needle cap 30 according to another embodiment of the present invention. The needle cap 30 includes a flow path 33 which is connected to two needle connecting parts 31. In addition, the needle cap 30 differs from the needle cap 10 in that a threaded part 35 is arranged in the needle connecting part 31. By arranging a clamp to the flow path 33, it is possible to prevent air from being mixed into the other needle and the blood circuit even after removing one of the needles.

The threaded part 35 has a shape corresponding to the thread of the needle. Therefore, a thread with a shape which latches with the threaded part 35 is also included in needle which is used in the present embodiment. By rotating the needle in a range of 30° or more and 180° or less, the needle can be attached to and detached from the needle connecting part 31. It is preferred that the needle can be attached to and detached from the needle connecting part 31 in a rotation angle range of 45° or more and 90° or less. By arranging the threaded part 35 to the needle connecting part 31 in the needle cap 30, it is possible to prevent the needle from falling out of the needle connecting part 31. Since the remaining structure is the same as the needle cap 10 described above, a detailed explanation is omitted. Furthermore, it is also possible to arrange the needle cap 20 described above with a structure having a threaded part 35. In addition, it is also possible to apply the modified example in which each needle has a different thickness described above.

Figure 6:
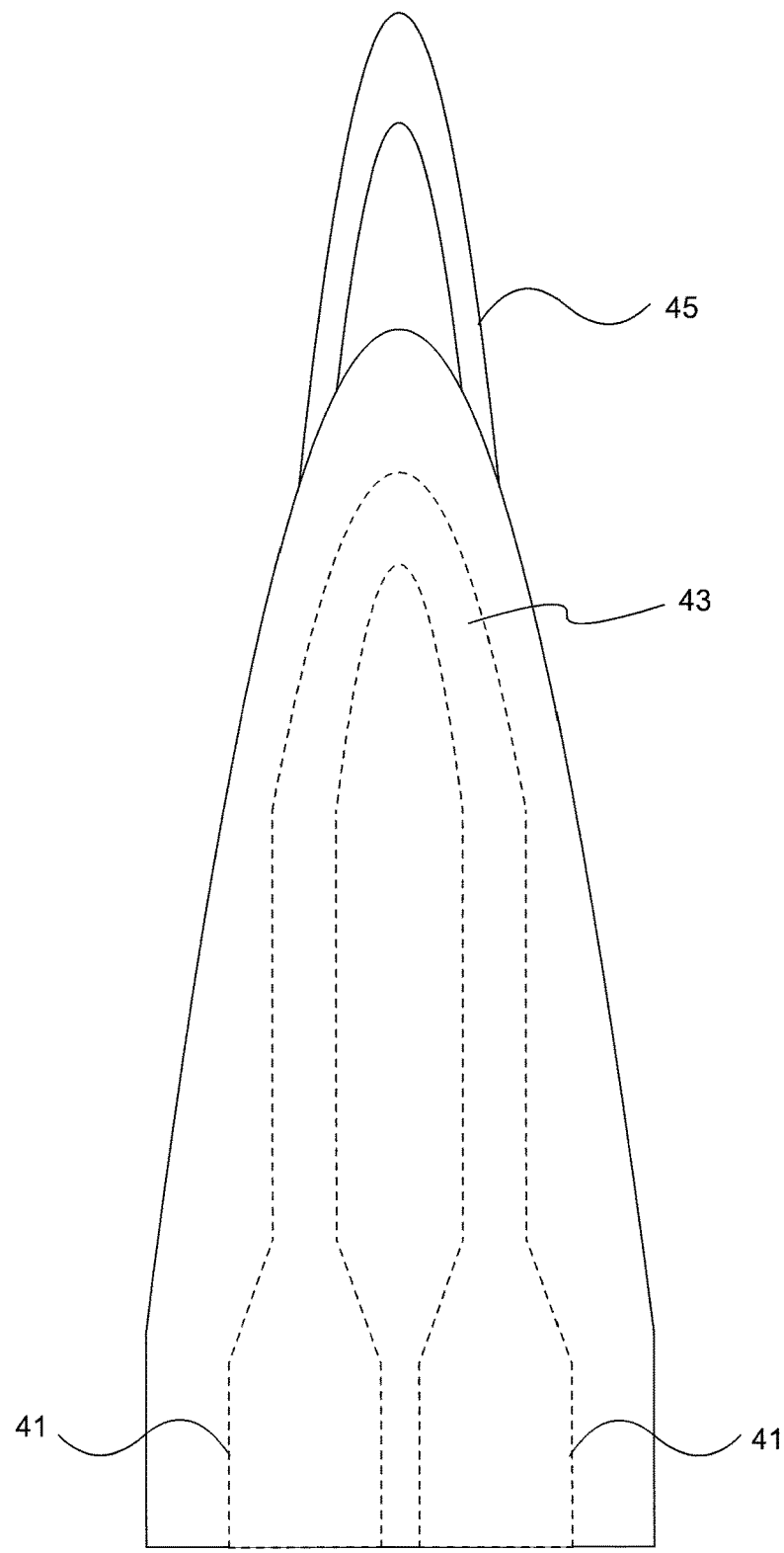
FIG. 6 is a schematic diagram of a needle cap according to one embodiment of the present invention.

FIG. 6 is a schematic diagram of a needle cap 40 according to another embodiment of the present invention. The needle cap 40 has two needle connecting parts 41 and a flow path 43 which connects to the two needle connecting parts 41. In addition, the needle cap 40 differs from the needle cap 10 in that a locking part 45 for locking an infusion stand is arranged.

The locking part 45 is preferred to be arranged in the flow path 43 side (tip end part) of the needle cap 40 but is limited to this. The locking part 45 is preferred to have a structure so that it can be hooked on the infusion stand and may have a ring shaped structure. The size of the locking part 45 is not particularly limited as long as it can be hooked to the infusion stand and has the size and strength so that it is possible to lock the needle cap 40 in which a needle is connected to the artery side blood circuit and the vein side blood circuit. Since the remaining structure is the same as the needle cap 10 described above, a detailed explanation is omitted. Furthermore, it is also possible to arrange the needle cap 20 and the needle cap 30 described above with a structure including the locking part 45. In addition, it is also possible to apply the modified example in which each needle has a different thickness described above.

FIG. 7A is a schematic diagram showing a dialysis circuit priming device 200 arranged with a with butterfly needle 219 according to another embodiment of the present invention, and FIG. 7B is a schematic diagram showing a dialysis circuit priming device 300 arranged with the butterfly needle 219 according to another embodiment of the present invention.

The butterfly needle 219 has a pair of wing parts 218. The dialysis circuit priming device 200 has a structure in which the needle cap 10 described above is arranged with the butterfly needle 219. In the dialysis circuit priming device 200, the wing parts 218 of two butterfly needles 219 are arranged to be parallel or substantially parallel so that each of the wing parts 218 of two butterfly needles 219 do not to interfere. Furthermore, it is also possible to use the needle cap 20 or the needle cap 40 described above instead of the needle cap 10. In addition, it is also possible to apply the modified example in which each needle has a different thickness described above.

On the other hand, in the dialysis circuit priming device 300, the needle connecting part 51 is arranged in the needle cap 50 at a distance so that the wing parts 218 of the two butterfly needles 219 do not interfere. The flow path 53 is not particularly limited as long as it has a length which allows the two needle connecting parts 51 to be connected. Since the remaining structure is the same as the needle cap 10 described above, a detailed explanation is omitted. Furthermore, the needle cap 50 may be arranged with a film 25 explained in the needle cap 20, the threaded part 35 explained in the needle cap 30, or the locking part 45 explained in the needle cap 40, or may be arranged with a combination of these. In addition, it is also possible to apply the modified example in which each needle has a different thickness described above.

Furthermore, in the embodiments described above, although an example is shown in which two needles are arranged in the needle cap according to the present invention, the present invention is not limited to this, and one of the artery side connecting part 1121 and the vein side connecting part 1161 may be directly connected to the needle connecting part without passing through the needle.

FIG. 9A is a schematic diagram of a needle cap 70 according to another embodiment of the present invention. The needle cap 70 includes two needle connecting parts 71 and a flow path 73 which is connected to the two needle connecting parts 71. Although an example having an arrangement in which the two needle connecting parts are parallel or substantially parallel is shown in the embodiment described above, the needle cap 70 has an arrangement in which the two needle connecting parts 71 are facing each other. As a result, the flow path 73 has a shape which linearly connects the two needle connecting parts 71. The needle cap 70 having such a structure can also be integrally molded. For example, it is possible to be formed by preparing a cylindrical needle cap and connecting the tip end parts of the needle caps.

This type of needle cap 70, for example, can also be carried out by a modified example such as the needle cap 80 shown in FIG. 9B. The needle cap 80 includes a flow path 83 which is connected to the two needle connecting parts 81. The flow path 83 has a structure in which a diameter becomes narrower from one needle connecting part 81 toward the center of the flow path 83, and the diameter becomes thicker from the center of the flow path 83 towards the other needle connecting part 81.

In addition, it is also possible to be carried out by a modified example such as a needle cap 90 shown in FIG. 10A. The needle cap 90 includes two needle connecting parts 91 and a flow path 93 which is connected to the two needle connecting parts 91. The flow path 93 has a structure in which the diameter becomes narrower from one of the needle connecting parts 91 to the center of the flow path 93, and the diameter becomes thicker from the center of the flow part 93 to the other needle connecting part 91. Here, the needle cap 90 is different to the needle cap 80 in that the flow path 93 has a curved cross-section with respect to the center axis of the flow path 93, whereas the needle cap 80 is arranged with a flow path 83 having a linear cross-sectional shape.

Furthermore, the needle cap 70 to the needle cap 90 described above, can be implemented as a modified example having each needle with different thicknesses as explained in the dialysis circuit priming device 400. FIG. 10B is a schematic diagram for explaining a dialysis circuit priming device 500 as a modified example. The dialysis circuit priming device 500 is arranged with a needle 519a and a needle 519b having different thicknesses in the needle cap 510. Here, since the flow path 513 connects the needle connecting part 511a which is arranged with a thick needle 519a and the needle connecting part 511b which is arranged with a thin needle 519b, it may have a structure in which the diameter becomes smaller from the needle connecting part 511a towards the needle connecting part 511b. The dialysis circuit priming device having an arrangement in which two needle connecting parts according to the present invention face each other is not limited to this structure, any of the needle cap 70 to the needle cap injections 90 can be applied.

In addition, a film for sealing the flow path explained in the needle cap 20 may be arranged in a needle connecting part in the dialysis priming device according to the present invention having an arrangement in which two needle connecting parts face each other. Furthermore, the dialysis circuit priming device according to the present invention having an arrangement in which two needle connecting parts face each other may have a structure in which a threaded part is arranged on the needle connecting part explained in the needle cap 30.

Although an example of the needle cap according to the present invention described above was explained having a structure in which two needle connecting parts and a flow path connecting the two needle connecting parts are integrally formed, the needle cap according to the present invention is not limited to this structure. An explanation is given below of another modified example of a needle cap according to the present invention.

FIG. 11A and FIG. 11B are schematic diagrams for explaining a dialysis circuit priming device 600 according to one embodiment of the present invention. FIG. 11A shows the dialysis circuit priming device 600, and FIG. 11B shows a cross sectional view (upper diagram) taken along the center line of FIG. 1A and shows a side surface view (lower diagram) seen from the center line direction. The dialysis circuit priming device 600 is arranged with a needle cap 630a including a needle connecting part 631a arranged with a needle 619a, and a needle cap 630b including a needle connecting part 631b arranged with a needle 619b. The dialysis circuit priming device 600 is further arranged with a joint member 610 for connecting the needle cap 630a and the needle cap 630b.

One end of the joint member 610 is locked with the needle cap 630a, and the other end is locked with the needle cap 630b. Each locking part 611 of the needle cap 630a and the needle cap 630b are respectively arranged at both ends of the joint member 610. Joint member 610 has a hollow structure including a flow path 613 which connects the locking parts 611 at both end parts.

The joint member 610 is, for example, made of resin, and can be formed by a known resin which is used for the needle cap for medical application. In addition, it is preferred that the resin which forms the flow path 613 part has flexibility. By providing the flow path 613 part with flexibility, in the case where the needle 619a, the needle 619b and the flow path 613 are filled with saline, by clamping the flow path 613, it is possible to prevent the entry of air into the other needle 619 even if the needle 619a or the needle 619b is removed from the needle cap 630a or needle cap injections 630b which connect the needles 619a or needle 619b. In the joint member 610 according to the present invention, the flow blocking means is not limited to this structure, and the flow path 613 may also be arranged with a valve (not shown in the diagram).

The needle cap 630a is arranged with a needle connecting part 631a which is arranged with a needle 619a. In addition, the needle cap 630b is arranged with a needle connecting part 631b which is arranged with a needle 619b. A flow path 633a is arranged at the tip end part of the needle 619a. In addition, a flow path 633b is arranged at the tip end part of the needle 619b. By arranging the needle cap 630a and the needle cap 630b at both ends of the joint member 610, the flow path 633a and the flow path 633b are connected to the flow path 613 to form one flow path.

The tip end part of the needle cap 630a and the needle cap 630b has a shape which locks with the lock part 611 of the joint member 610. The needle cap 630a and the needle cap 630b may be a cylindrical needle cap, and in this case, a tip end part of the needle cap 630a and the needle cap 630b has a cylindrical shape. The needle cap 630a and the needle cap 630b are, for example, made from a resin and can be formed by a known resin which is used for the needle caps for medical application.

In addition, the dialysis circuit priming device 600, as explained in the dialysis circuit priming device 400, can be carried out as a modified example in which the needle cap 630a and the needle cap 630b have needles with different thicknesses. The cylindrical needle cap does not have any difference (or almost identical) in the thickness (diameter) of the tip end part even if the thickness of the needles is different. As a result, both ends of the locking part 611 of the joint member 610 may be the same diameter. In addition, when one end of the locking part 611 of the joint member 610 has a different thickness (diameter) than the other end, it is possible to lock even in the case when the thickness (diameter) of the tip end parts of the needle cap 630a and the needle cap 630b are different.

In the present embodiment, in the case when a cylindrical needle cap is used for the needle cap 630a and the needle cap 630b, the tip end part of the needle cap (from the tip to the open position of the flow path 633) is cut and the tip end part of the needle cap is opened. The opened tip end part of the needle cap (needle cap 630a and needle cap 630b) respectively lock the both end parts of the locking part 611 of the joint member 610.

In addition, a film which seals the flow path explained in the needle cap 20 may be arranged in the dialysis circuit priming device 600 according to the present invention having an arrangement in which the needle connecting part 631a and the needle connecting part 631b face each other. Furthermore, the dialysis circuit priming device 600 may have a structure in which a threaded part is arranged on the needle connecting part explained in the needle cap 30.

Although an example was explained in which two needle caps 630a and 630b are applied with a cylindrical cap in the dialysis circuit priming device 600 according to the present invention described above, the needle cap according to the present invention is not limited to this structure. An explanation is given below of a modified example of the dialysis circuit priming device 600.

Figure 12A:
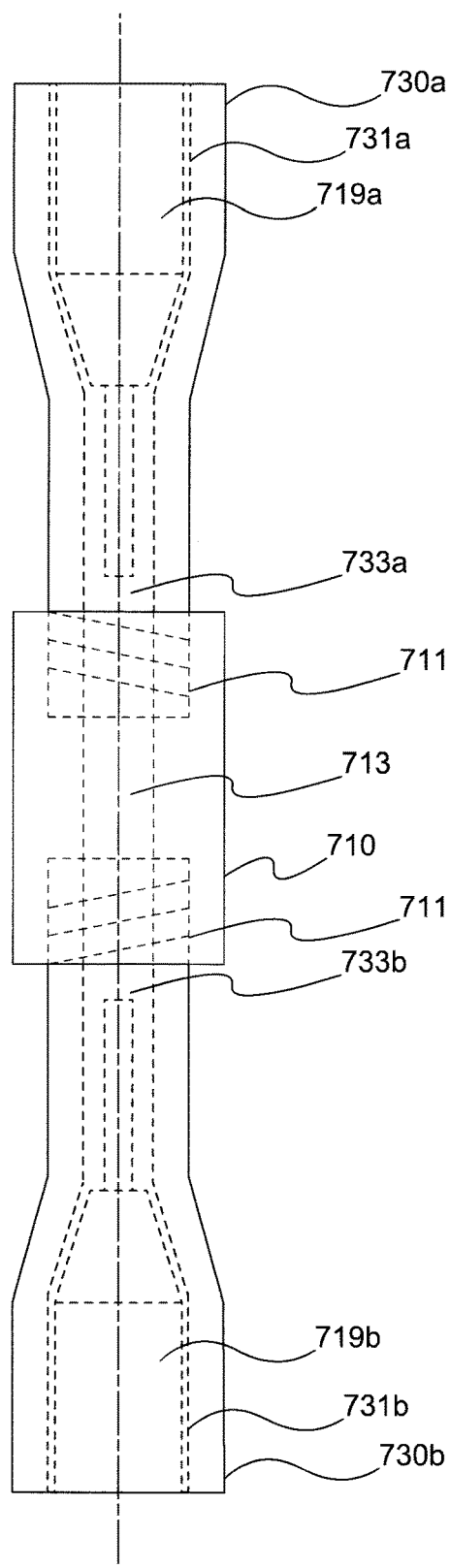
FIG. 12A shows a dialysis circuit priming device 700.
Figure 12B:
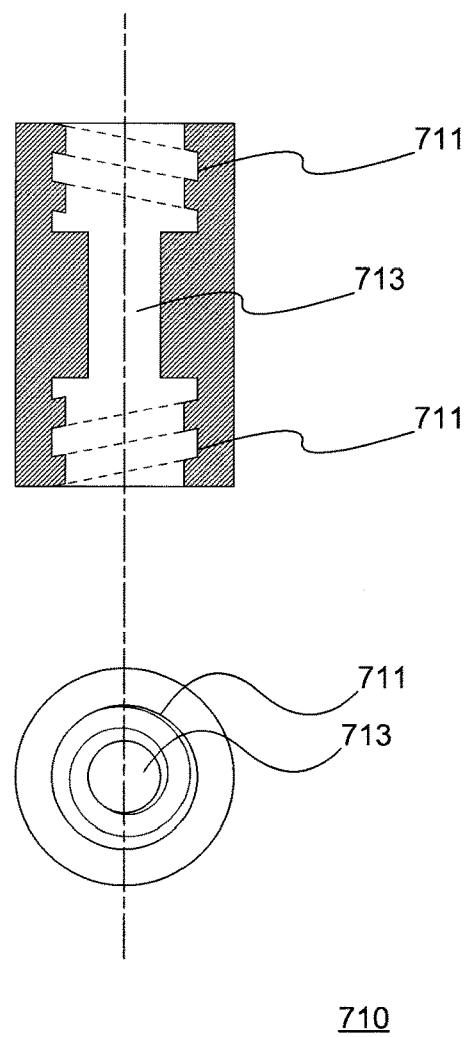
FIG. 12B shows a cross sectional diagram taken along a center line of FIG. 12A (upper diagram) and a side surface diagram as seen from the center line direction (lower diagram).

FIG. 12A and FIG. 12B are schematic diagrams for explaining a dialysis circuit priming device 700 according to one embodiment of the present invention. FIG. 12A shows the dialysis circuit priming device 700, and FIG. 12B shows a cross sectional view (upper diagram) taken along the center line in FIG. 12A and a side surface view (lower diagram) seen from the center line direction. The dialysis circuit priming device 700 includes a needle cap 730a having a needle connecting part 731a arranged with a needle 719a, and a needle cap 730b having a needle connecting part 731b arranged with a needle 719b. The dialysis circuit priming device 700 is further arranged with a joint member 710 for connecting the needle cap 730a and the needle cap 730b.

One end of the joint member 710 locks with the needle cap 730a and the other end locks with the needle cap 730b. The locking part 711 which respectively locks the needle cap 730a and the needle cap 730b is arranged at both ends of the joint member 710. The joint member 710 has a hollow structure including a flow path 713 which connects the locking part 711 at both end parts. In the present embodiment, the locking part 711 has a threaded part. The threaded part of the locking part 711 has a shape corresponding to the threaded part of the needle cap 730a and the needle cap 730b described herein. By rotating the needle cap 730a and the needle cap 730b in a range of 30° or more and 180° or less, it is possible to attach and detach the needle cap 730a and the needle cap 730b to the joint member 710. It is preferred that it is possible to attach and detach the needle cap 730a and the needle cap 730b to the joint member 710 in a range of rotation angle of 45° or more and 90° or less. The dialysis circuit priming device 700 is arranged with the threaded part to the locking part 711 of the joint member 710, and thereby the needle cap 730a and the needle cap 730b can be prevented from falling from the joint member 710. Since the remaining structure is the same as the dialysis circuit priming device 600 described above, a detailed explanation is omitted.

Figure 13:
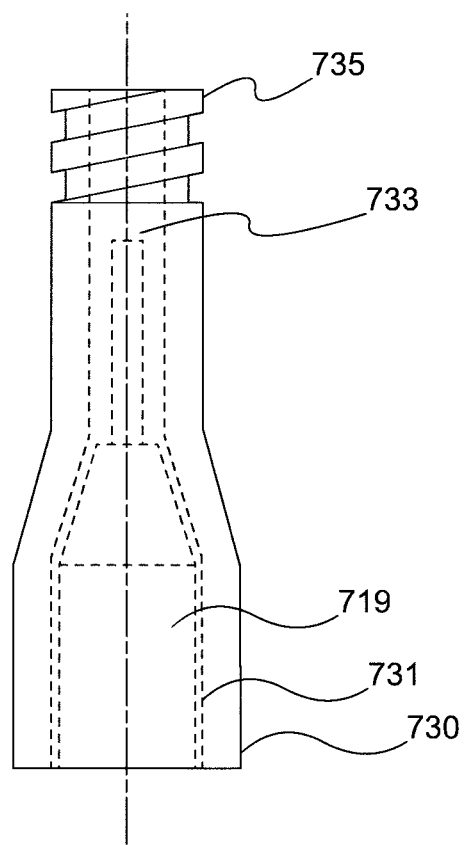
FIG. 13 is a schematic diagram for explaining a needle cap 730 according to one embodiment of the present invention.

FIG. 13 is a schematic diagram for explaining a needle cap 730 according to one embodiment of the present invention. The needle cap 730a is arranged with a needle connecting part 731a including a needle 719a. In addition, the needle cap 730b is arranged with a needle connecting part 731b including a needle 719b. A flow path 733a is arranged at the tip end part of the needle 719a. In addition, a flow path 733b is arranged at the tip end part of the needle 719b. By arranging the needle cap 730a and the needle cap 730b at both ends of the joint member 710, the flow path 733a and the flow path 733b are connected to form one flow path.

The tip end part of the needle cap 730a and the needle cap 730b includes a threaded part 735 which locks with the locking part 711 of the joint member 710. The needle cap 730a and the needle cap 730b are, for example, made of a resin, and can be formed by a known resin used for needle cap for medical applications. The opening of the flow path 733 may be sealed by placing a cap on the threaded part 735 during use.

In addition, the dialysis circuit priming device 700, as explained in the dialysis circuit priming device 400, can be carried out as a modified example in which the needle cap 730a and the injection needle cap 730b have a needles with different thicknesses. Both end parts of the locking part 711 of the joint member 710 may have the same diameter. In addition, by making one end of the locking part 711 a different thickness (diameter) than the other end, it is possible to lock even in the case where the thickness (diameter) of the tip end parts of the needle cap 730a and the needle cap 730b are different.

In addition, a film which seals the flow path explained in the needle cap 20 may be arranged in the dialysis circuit priming device 700 according to the present invention having an arrangement in which the needle connecting part 731a and the needle connecting part 731b face each other. Furthermore, the dialysis circuit priming device 700 may have a structure in which a threaded part is arranged on the needle connecting part explained in the needle cap 30.

Although an example in which a needle and a flow path are connected by adhering to a needle hub which supports a needle in the needle cap according to the present invention is explained in the embodiment described above, the needle cap according to the present invention is not limited to this. As a specific example, a different embodiment to the embodiment described above is explained below.

Figure 14A:
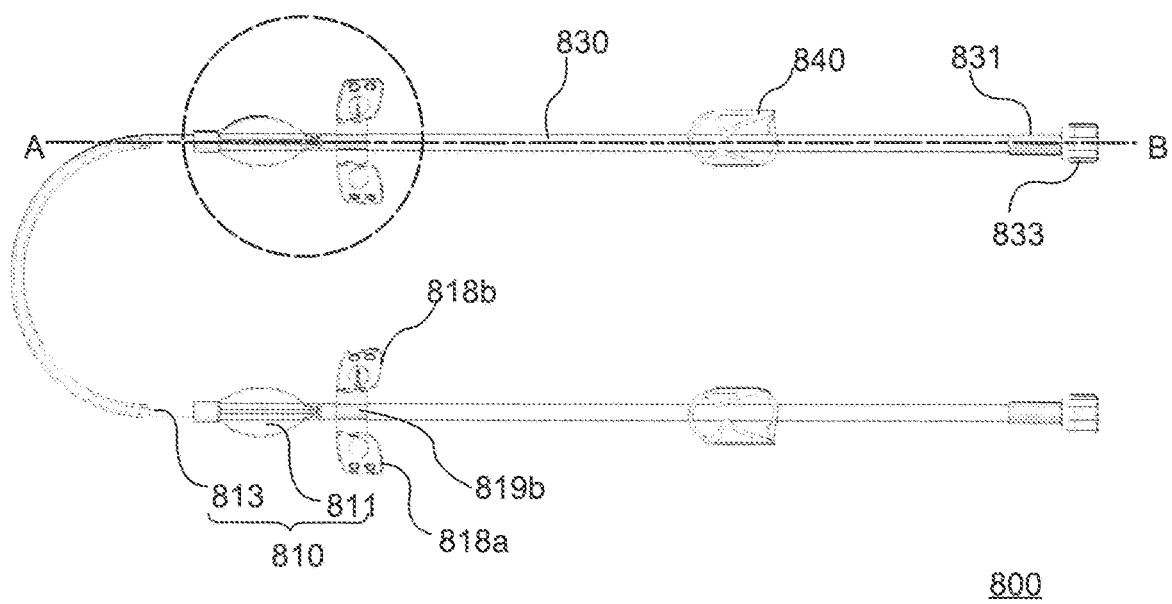
FIG. 14A is a schematic diagram of a dialysis circuit priming device 800 according to one embodiment of the present invention.
Figure 14B:
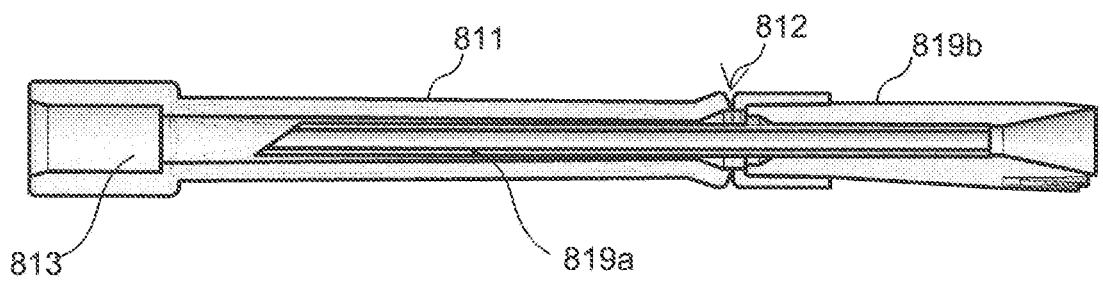
FIG. 14 B is a cross sectional diagram in a segment AB near a needle connecting part 811 surrounded by the broken line in FIG. 14A.

FIG. 14A is a diagram showing a dialysis circuit priming device 800, and FIG. 14BB is a cross sectional diagram of a segment AB in the vicinity of the needle connecting part 811 surrounded by a broken line shown in FIG. 14A The dialysis circuit priming device 800 is arranged with a needle cap 810 having a flow path 813 which is connected to two needle connecting parts 811 which are arranged respectively with a needle 819. Although a needle 819 is preferred to be a butterfly shape as an example from the view point of simplicity of puncture procedure, it is not limited to this shape. The needle 819 has a wing part 818a and a wing part 818b on the needle hub 819b for holding the needle body 819a. In the present embodiment, an example of the dialysis circuit priming device 800 having a tube 830 is shown. A first end of the tube 830 is connected to the needle hub 819*b*, and a second end is connected to a connector 831. In addition, the connector 831 is protected by a cap 833. In addition, the tube 830 may be arranged with a Robert clamp 840 for example.

In one embodiment, since the flow path 813 is formed from a tube and has flexibility, it is possible to freely change each arrangement of the two needle bodies 819*a* via the flow path 813, it is possible to hook it to an infusion stand, and it is possible to reduce the size of the packaging. As a result, the flow path 813 is preferred to have any length so that it can be hooked to the infusion stand, and has a hardness so that the flow path 813 is not blocked when the tube bends when hooked to the infusion stand. In the present embodiment, the flow path 813 and the needle hub 819*b* are fixed at each end of the needle connecting part 811, and the needle connecting part 811 has an internal structure that covers the entire needle body 819*a*. The needle connecting part 811 is formed by a rigid member, prevents the needle body 819*a* from piercing the needle connecting part 811, and prevents the needle body 819*a* from being exposed to the exterior. In addition, the needle connecting part 811 includes a weak part 812 in the vicinity of the needle hub 819*b*. The weak part 812 is a weak region which has lower strength than other parts of the needle connecting part 811, for example, a part having a thin part, but is not limited to this, and may have a structure or may be a material capable of separating the needle connecting part 811 from the needle 819. Furthermore, although the needle connecting part 811 may be molded including a weak part, it may also be formed by fixing or assembling a plurality of members, or a part which is assembled or fixed may be a weak part. In addition, although it is preferred to provide a flexible tube as a flow path 813, it is not essential. For example, it is possible to hook to an infusion stand by forming the entire flow path 813 from a hard material as an arrangement in which two needle bodies 819*a* are in parallel or substantially parallel.

In addition, the tube 830 is formed by a known resin material and is not particularly limited. The connector 831 is a terminal for connecting to a blood circuit and is not particularly limited. In addition, the present invention may be directly connected to an end part of the blood circuit without going through the connector 831. In addition, the cap 833 is connected to the connector 831, and can be removed from the connector 831 when the connector 831 is connected to a blood circuit, and is not particularly limited.

Figure 15A:
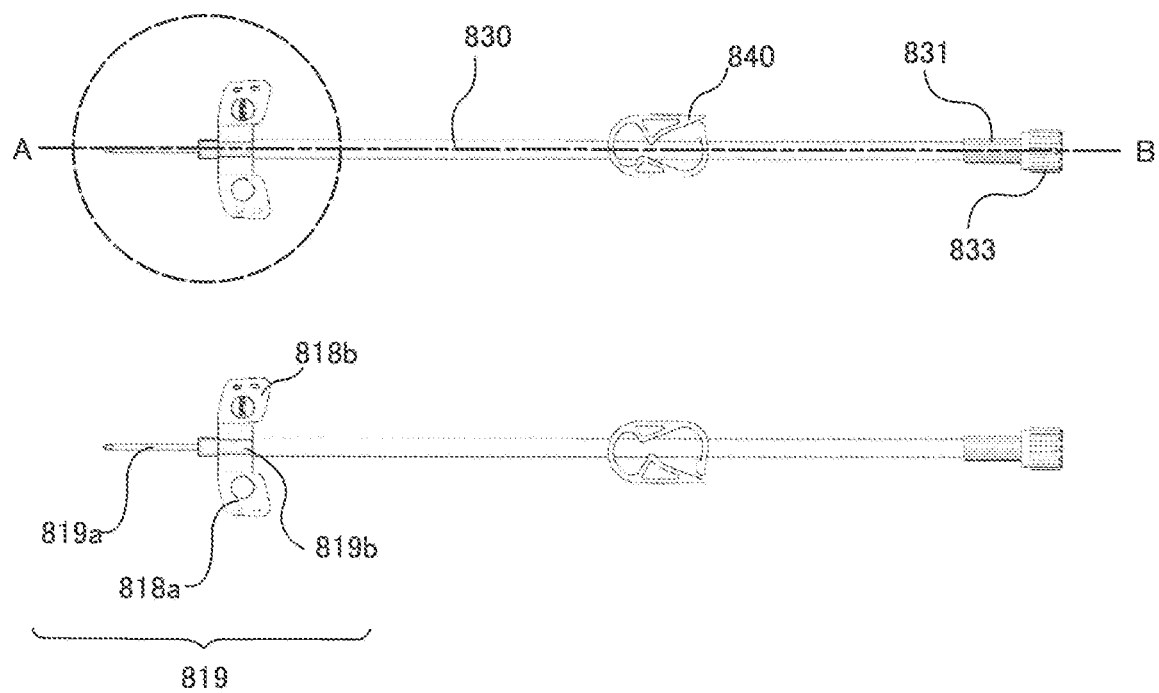
FIG. 15A is a schematic diagram showing a state in which a needle cap 810 is removed from the dialysis circuit priming device 800 according to one embodiment of the present invention.
Figure 15B:
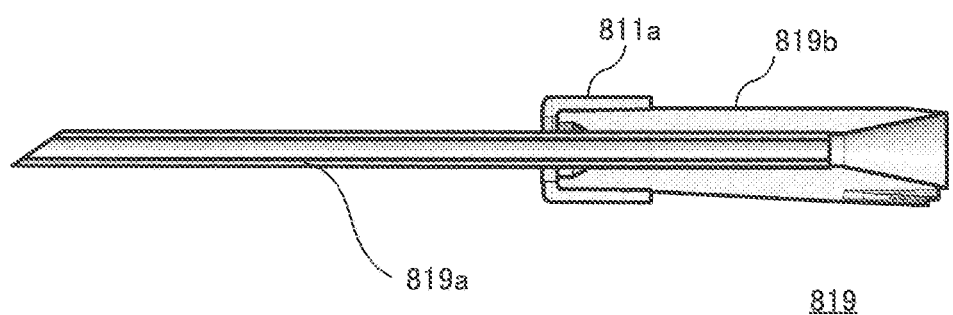
FIG. 15B is a cross sectional diagram of a needle 811 in a segment AB surrounded by the broken line in FIG. 15A.

FIG. 15A is a schematic diagram showing a state in which the needle cap 810 is removed from the dialysis circuit priming device 800 according to one embodiment of the present invention. FIG. 15B is a cross sectional diagram in the segment AB of the needle 819 surrounded by a broken line in FIG. 15A. In one embodiment, when the needle cap 810 is removed, it is preferred that a part of the needle connecting part 811 which is broken by the weak part 812 is located in the vicinity of the needle hub 819*b*. That is, it is particularly preferred that a part of the needle connecting part 811 which is broken by the weak part 812 is adjacent to the needle hub 819*b* for connecting to the needle body 819*a*, and in the present embodiment, a part of the needle connecting part 811 which is broken by the weak part 812 is adjacent to the tip end of the needle hub 819*b*. When the needle cap 810 is removed, by adopting such a structure, it becomes difficult for part of the needle connecting part 811 to obstruct a puncture and handling is easily performed.

Figure 16A:
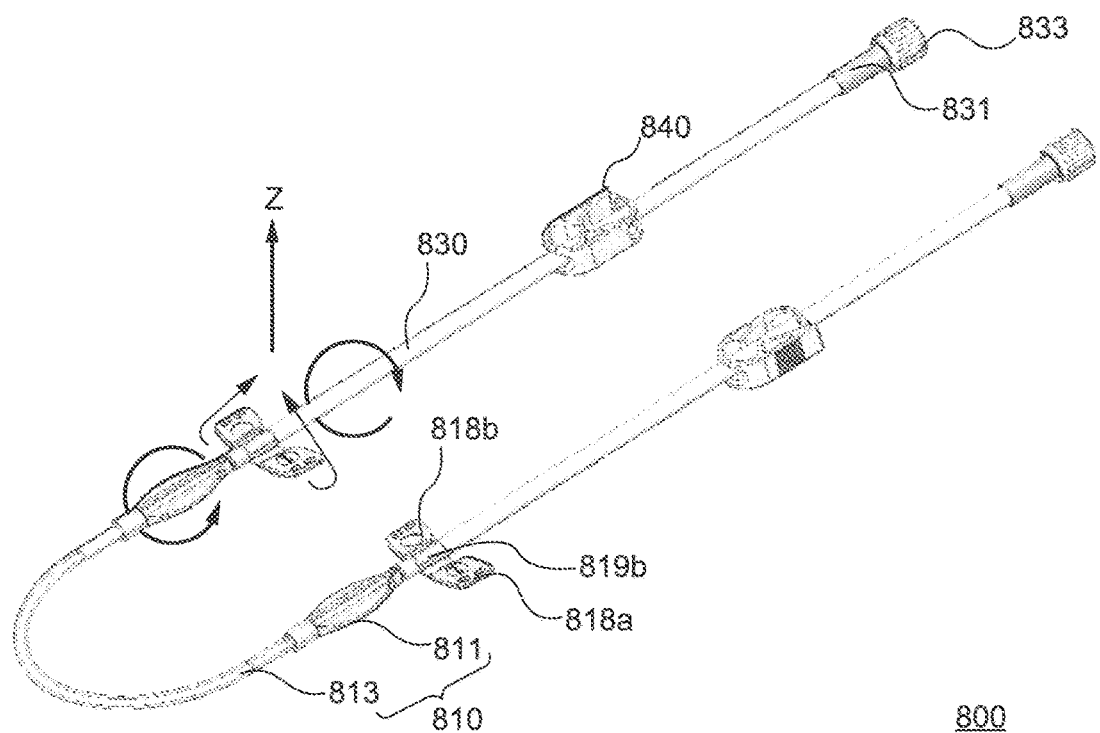
FIG. 16A is a schematic diagram for explaining a method of removing a needle cap 810 from the dialysis circuit priming device 800 according to one embodiment of the present invention.
Figure 16B:
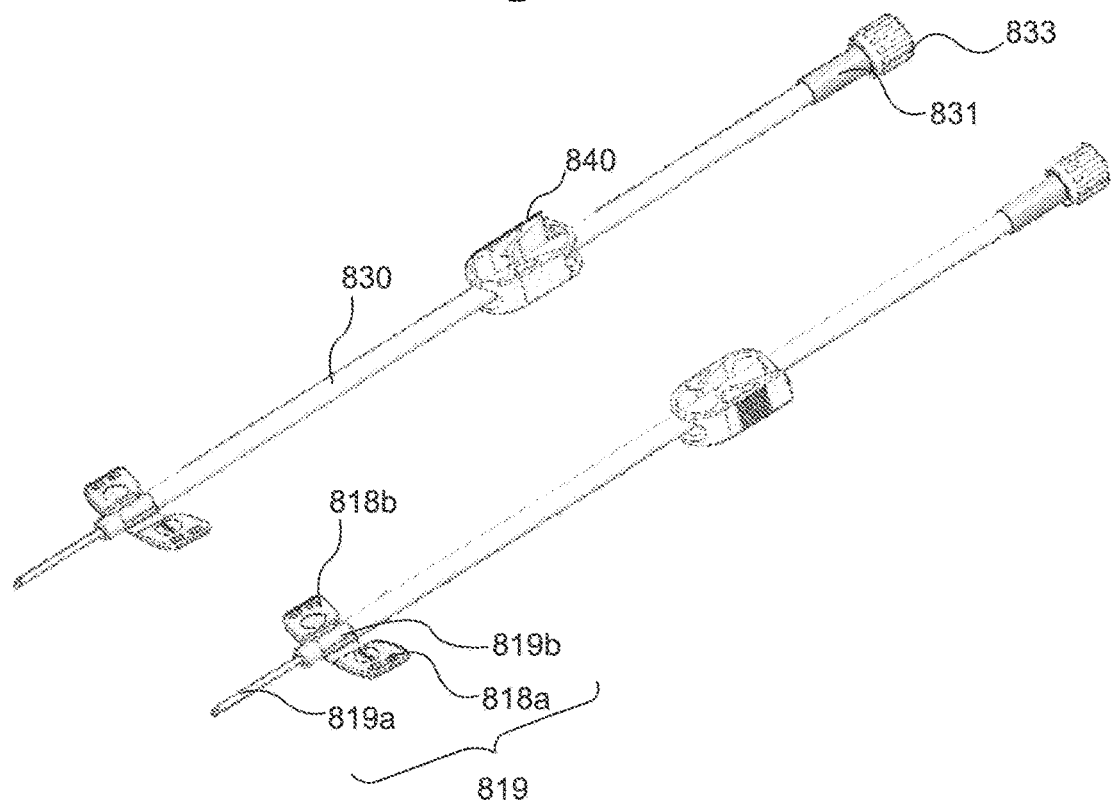
FIG. 16B is a schematic diagram showing a state in which the needle cap 810 is removed.

FIG. 16A is a schematic diagram for explaining a method of removing the needle cap 810 from the dialysis circuit priming device 800 according to one embodiment of the present invention. FIG. 16B is a schematic diagram showing a state in which the needle cap 810 is removed. In one embodiment, the weak part 812 is torn and the needle connecting part 811 can be separated from the needle 810 by relative rotation (either by rotating in one direction or twisting each in revere directions) while pulling the needle connecting part 811 and the needle 819.

For example, in the case where the needle 819 is a butterfly needle, the wing part 818*a* and wing part 818*b* may be held with one hand and bent in a direction substantially perpendicular (Z-direction in FIG. 16A) with respect to the wing part 818*a* and wing part 818*b*, and by holding the needle connecting part 811 with the other hand and performing relative rotation, it is possible to tear the weak part 812 and separate the needle connecting part 811 from the needle 819. As a result, in one embodiment, the needle connecting part 811, for example, has a flat plate shaped structure which is easily held, and the weak part 812 is easy to tear which is preferred. Specifically, each end part of the needle connecting part 811 in the present embodiment is a cylindrical part, and a flow path or needle hub is inserted into each end part. The outer surface has a flat plate part between cylindrical parts. The flat plate part has a hollow shape having a tapered structure which decreases in diameter toward the needle hub side, and the needle body 819*a* is located inside. The external shape of the flat plate part has a planar view elliptical shape and a side view biconcave shape from the viewpoint of usability. In addition, the flat plate part has a surface that intersects a surface of the wing part 818*a* and wing part 818*b* in a state held by one hand, and the flat plate shaped part is easily rotated in a state where the wing parts are held with one hand. Furthermore, the flat plate shaped part has a structure having a surface parallel to the wing part 818*a* and wing part 818*b* in a state before being held with a hand. Furthermore, the shape of the needle connecting part 811 may be a structure which is easily held and is easy to tear the weak part 812 but is not limited to this shape. For example, a flat plate part can be a cylindrical shape which has ribs. In addition, the needle connecting part 811 is preferred to be easy to hold and is formed of a material having sufficient rigidity in order to protect the needle body 819*a*.

Since the dialysis circuit priming device 800 according to the present embodiment has the needle connecting part 811 fixed to the needle hub 819*b*, it is possible to safely perform priming without the needle body 819*a* being released from the needle connecting part 811 by pressure when priming. In addition, since the needle connecting part 811 includes the weak part 812, it is easy to separate the needle 819 from the needle connecting part 811 after the priming.

Figure 17:
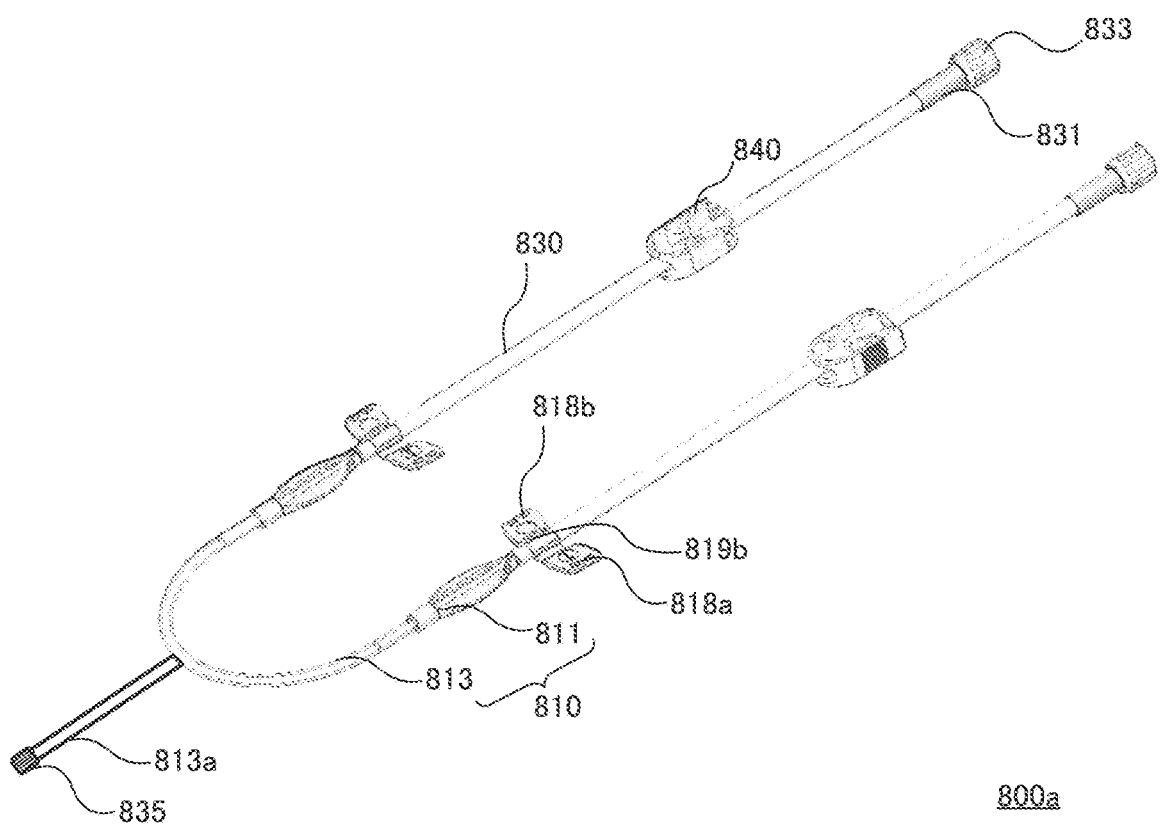
FIG. 17 is a schematic diagram of a dialysis circuit priming device 800a according to a modified example of the present invention.

FIG. 17 is a schematic diagram of a dialysis circuit priming device 800*a* according to a modified example. The dialysis circuit priming device 800*a* is different from the dialysis circuit priming device 800 in that it includes a drain path 813*a* in a flow path 813. In one embodiment, a cap 835 is arranged at the end part of the drain path 813*a*. By arranging the drain path 813*a*, it is possible to discharge a fluid from the flow path 813. Since it is possible to use the same structure as the dialysis circuit priming device 800 described above for the remaining structure, a detailed explanation thereof is omitted.

Figure 18:
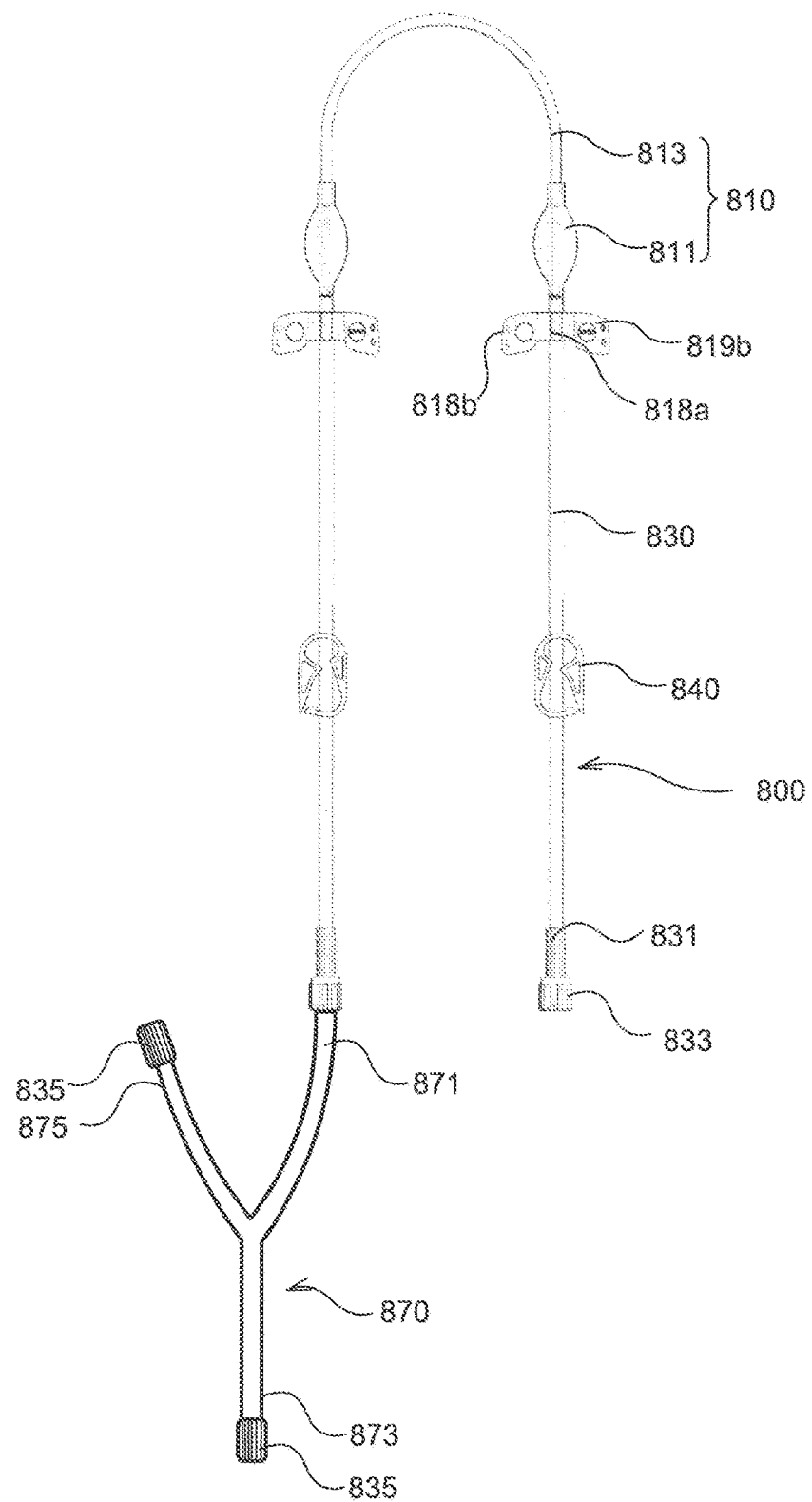
FIG. 18 is a schematic diagram for explaining a modified example using the dialysis circuit priming device 800 of the present invention.

FIG. 18 is a schematic diagram for explaining a modified example using a dialysis circuit priming device 800. In this modified example, a branch tube 870 is connected to a connector 831 of the dialysis circuit priming device 800. For example, a first end part 871 of the branch tube 870 is connected to the connector 831, a second end part 873 is connected to the blood circuit, and it is possible to use the third end part 875 as a drain path. Since the same structure as the dialysis circuit priming device 800 described above can be used for the remaining structure, a detailed explanation is omitted.

According to the present invention, a needle cap and a dialysis circuit priming device are provided with increased safety and convenience in the cleaning and priming of a blood circuit.

What is claimed is:

1. A dialysis circuit priming device comprising:
   a butterfly shaped needle including two wing parts;
   a needle connecting part connected to the butterfly shaped needle; and
   a flow path connected to the needle connecting part and capable of connecting the needle connecting part to another needle therethrough,
   wherein the needle connecting part has a weak part to allow the needle connecting part to be divided so as to draw the butterfly shaped needle from the needle connecting part, and
   wherein the needle connecting part includes a cylindrical part and an outer surface having a flat plate part laterally extending from the cylindrical part.

2. The dialysis circuit priming device according to claim 1, further comprising:
   a film arranged in the needle connecting part to seal the flow path.

3. The dialysis circuit priming device according to claim 1, further comprising:
   a locking part to lock an infusion stand.

4. The dialysis circuit priming device according to claim 1, wherein the flow path is formed with a flexible tube.

5. The dialysis circuit printing device according to claim 1, further comprising a drain path included in the flow path.

6. A dialysis circuit priming device comprising:
   a first needle cap and a second needle cap, the first and second needle caps each having a tip end part and a base part, the base part having a needle connecting part, the needle connecting part being arranged with a needle;
   a joint member having two ends and two locking parts, one locking part of the two locking parts arranged at each end of the two ends; and
   a flow path connected to the needle connecting parts of the first needle cap and the second needle cap,
   wherein each tip end part of the first and second needle caps has an opening,
   wherein each tip end part of the first and second needle caps has a shape which locks with the locking parts of the joint member,
   wherein the joint member locks the tip end part of the first needle cap at one of the locking parts and the tip end part of the second needle cap at the other locking part of the two locking parts,
   wherein the needle includes a tip, a frustoconical part and a cylindrical part sequentially arranged,
   wherein the cylindrical part has a diameter larger than a diameter of the tip,
   wherein a diameter of the frustoconical part expands radially outward from the tip toward the cylindrical part,
   wherein each of the first and second needle caps has a cylindrical inner surface at the needle connecting part and a frustoconical inner surface connecting to the cylindrical inner surface,
   wherein a diameter of the frustoconical inner surface contracts radially inward from the cylindrical inner surface toward the tip end part, and
   wherein each needle connecting part of the first and second needle caps covers the cylindrical part of the needle.

7. The dialysis circuit priming device according to claim 6, further comprising:
   a shape of each tip end part of the first and second needle caps being a thread arranged on each tip end part of the first and second needle caps; and
   a threaded part arranged in each locking part of the locking parts of the joint member, each threaded part of each locking part having a shape corresponding to the thread of the first needle cap and the second needle cap.

8. A needle cap comprising:
   two ends;
   a needle connecting part arranged at one end of the two ends, the needle connecting part having a diameter larger than a diameter of the other end of the two ends, and the needle connecting part being capable of connecting a needle;
   a cylindrical inner surface at the needle connecting part;
   a frustoconical inner surface connecting to the cylindrical inner surface;
   an opening arranged at the other end of the two ends;
   a flow path connected to the opening; and
   a threaded part arranged at the other end of the two ends,
   wherein the needle includes a tip, a frustoconical part and a cylindrical part sequentially arranged,
   wherein a diameter of the frustoconical part expands radially outward from the tip toward the cylindrical part,
   wherein a diameter of the frustoconical inner surface contracts radially inward from the cylindrical inner surface toward the opening, and
   wherein the needle connecting part is capable of covering the cylindrical part of the needle.

9. The needle cap according to claim 8, wherein the threaded part is capable to lock with a locking part of a joint member to arrange a flow path between the needle cap and the joint member.

* * * * *